US009358813B2

(12) United States Patent
Yokozawa et al.

(10) Patent No.: US 9,358,813 B2
(45) Date of Patent: Jun. 7, 2016

(54) MEDIUM IDENTIFICATION DEVICE, IMAGE FORMING APPARATUS, METHOD OF IDENTIFYING MEDIUM, AND COMPUTER PROGRAM PRODUCT

(71) Applicants: Suguru Yokozawa, Kanagawa (JP); Nobuyuki Satoh, Kanagawa (JP); Mamoru Yorimoto, Kanagawa (JP); Kenji Morita, Tokyo (JP); Masayuki Fujii, Kanagawa (JP); Daisaku Horikawa, Kanagawa (JP)

(72) Inventors: Suguru Yokozawa, Kanagawa (JP); Nobuyuki Satoh, Kanagawa (JP); Mamoru Yorimoto, Kanagawa (JP); Kenji Morita, Tokyo (JP); Masayuki Fujii, Kanagawa (JP); Daisaku Horikawa, Kanagawa (JP)

(73) Assignee: RICOH COMPANY, LTD., Tokyo (JP)

( * ) Notice: Subject to any disclaimer, the term of this patent is extended or adjusted under 35 U.S.C. 154(b) by 0 days.

(21) Appl. No.: 14/812,045

(22) Filed: Jul. 29, 2015

(65) Prior Publication Data
US 2016/0031250 A1 Feb. 4, 2016

(30) Foreign Application Priority Data

Aug. 1, 2014 (JP) ................................. 2014-158015

(51) Int. Cl.
*B41J 29/393* (2006.01)
*B41J 11/00* (2006.01)

(52) U.S. Cl.
CPC .................... *B41J 11/009* (2013.01)

(58) Field of Classification Search
CPC ...................................................... B41J 11/009
See application file for complete search history.

(56) References Cited

U.S. PATENT DOCUMENTS

| 6,668,144 | B2 | 12/2003 | Maruyama |
| 7,130,573 | B2 | 10/2006 | Nakamori |
| 7,558,492 | B2 | 7/2009 | Aoki |
| 8,902,466 | B2 | 12/2014 | Satoh |
| 2005/0276198 | A1* | 12/2005 | Kokubo ................ B41J 11/009 369/53.22 |

(Continued)

FOREIGN PATENT DOCUMENTS

| JP | 2002-182518 | 6/2002 |
| JP | 2003-302885 | 10/2003 |

(Continued)

OTHER PUBLICATIONS

U.S. Appl. No. 14/565,182, filed Dec. 9, 2014.

(Continued)

*Primary Examiner* — Julian Huffman
(74) *Attorney, Agent, or Firm* — Oblon, McClelland, Maier & Neustadt, L.L.P

(57) ABSTRACT

A medium identification device identifies a type of a recording medium used for image formation. The medium identification device includes: a two-dimensional image sensor that captures an image of the recording medium; and an identifying unit that obtains a glossiness evaluation value indicating glossiness of the recording medium, a surface roughness evaluation value indicating surface roughness of the recording medium, and a coloring evaluation value indicating coloring of the recording medium, using image data of a specular reflection region reflecting specular reflection light from the recording medium and image data of a diffused reflection region reflecting diffused reflection light from the recording medium, the regions being in the image of the recording medium, and identifies the type of the recording medium by combining determination using the glossiness evaluation value, determination using the surface roughness evaluation value, and determination using the coloring evaluation value.

12 Claims, 27 Drawing Sheets

(56) References Cited

U.S. PATENT DOCUMENTS

| | | |
|---|---|---|
| 2012/0069411 A1 | 3/2012 | Satoh et al. |
| 2012/0236308 A1 | 9/2012 | Satoh |
| 2013/0027720 A1 | 1/2013 | Satoh |
| 2013/0027721 A1 | 1/2013 | Kobayashi et al. |
| 2013/0135484 A1 | 5/2013 | Satoh et al. |
| 2013/0208289 A1 | 8/2013 | Satoh et al. |
| 2013/0229671 A1 | 9/2013 | Yokozawa et al. |
| 2013/0242319 A1 | 9/2013 | Suzuki et al. |
| 2013/0242320 A1 | 9/2013 | Suzuki et al. |
| 2013/0242321 A1 | 9/2013 | Okada et al. |
| 2013/0242361 A1 | 9/2013 | Matsumoto et al. |
| 2013/0258368 A1 | 10/2013 | Shigemoto et al. |
| 2013/0258369 A1 | 10/2013 | Suzuki et al. |
| 2014/0218754 A1 | 8/2014 | Satoh et al. |
| 2015/0029257 A1* | 1/2015 | Isoda .................. B41J 11/009 347/19 |
| 2015/0070737 A1 | 3/2015 | Hirata et al. |
| 2015/0085305 A1 | 3/2015 | Suzuki et al. |
| 2015/0109646 A1 | 4/2015 | Yokozawa et al. |
| 2015/0146053 A1 | 5/2015 | Satoh et al. |
| 2015/0158309 A1 | 6/2015 | Fujii et al. |
| 2015/0162372 A1 | 6/2015 | Yorimoto et al. |

FOREIGN PATENT DOCUMENTS

| | | |
|---|---|---|
| JP | 2007-055814 | 3/2007 |
| JP | 2013-051671 | 3/2013 |

OTHER PUBLICATIONS

U.S. Appl. No. 14/789,015, filed Jul. 1, 2015.
U.S. Appl. No. 14/753,729, filed Jun. 29, 2015.

* cited by examiner

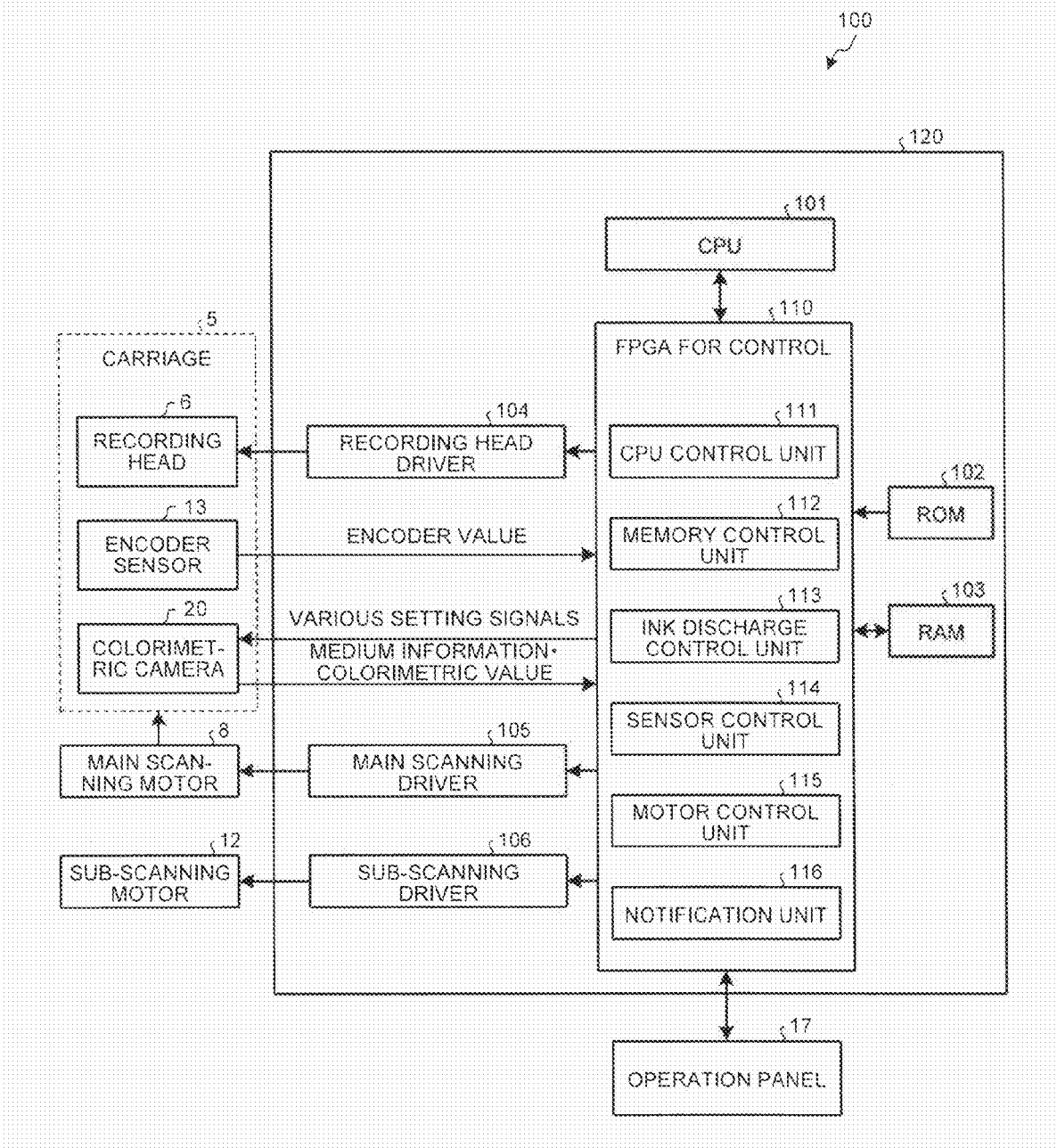

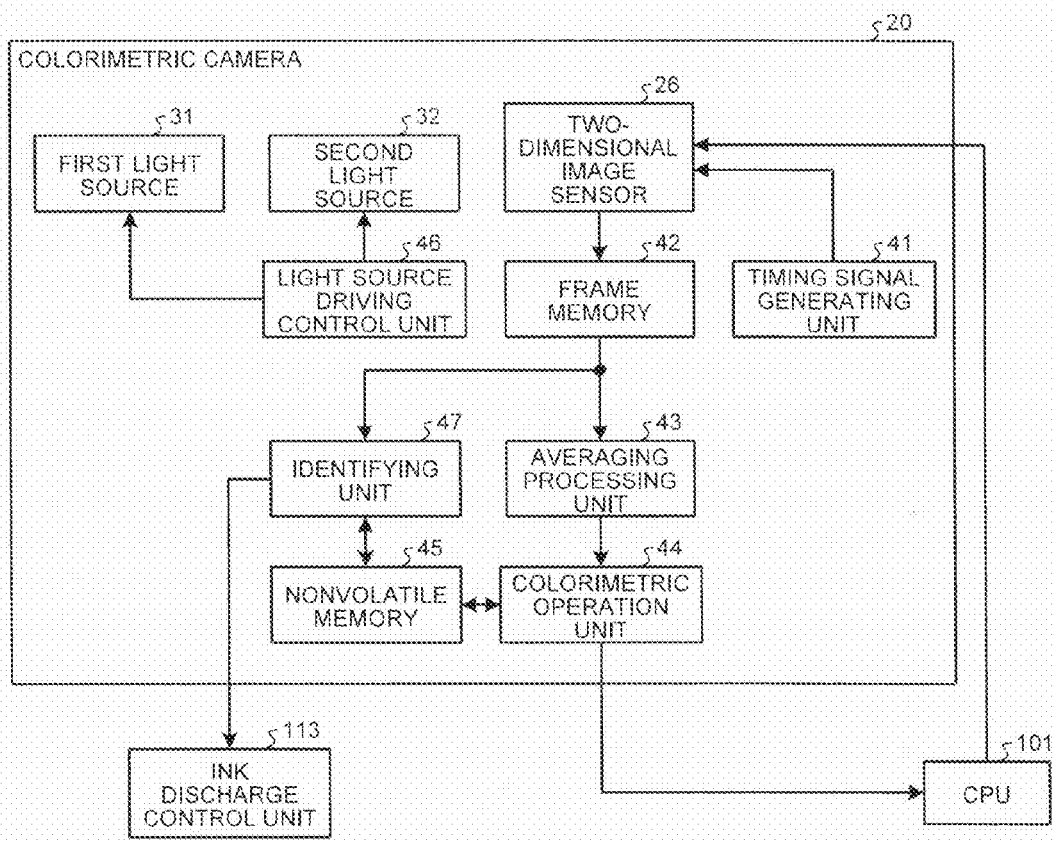

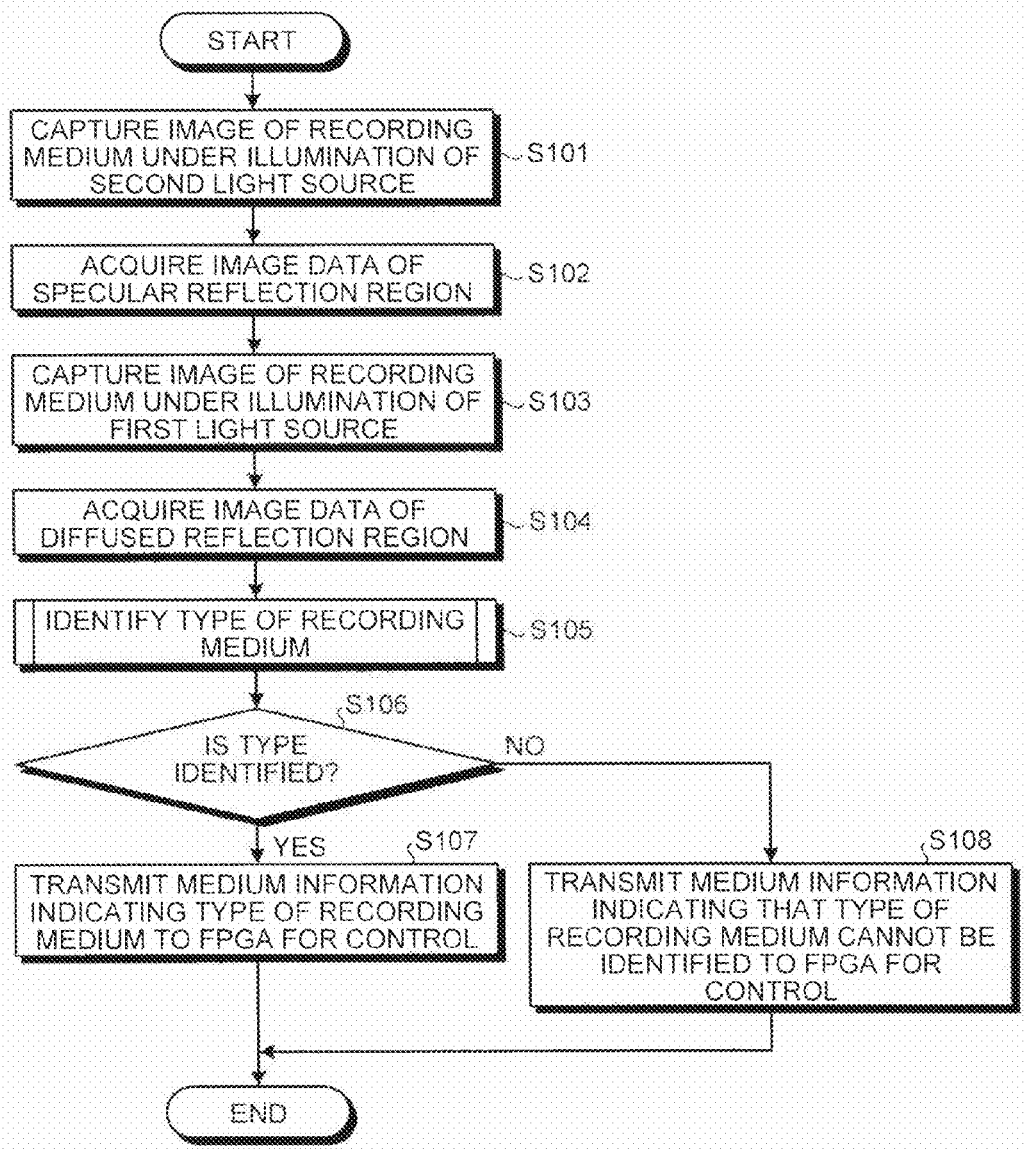

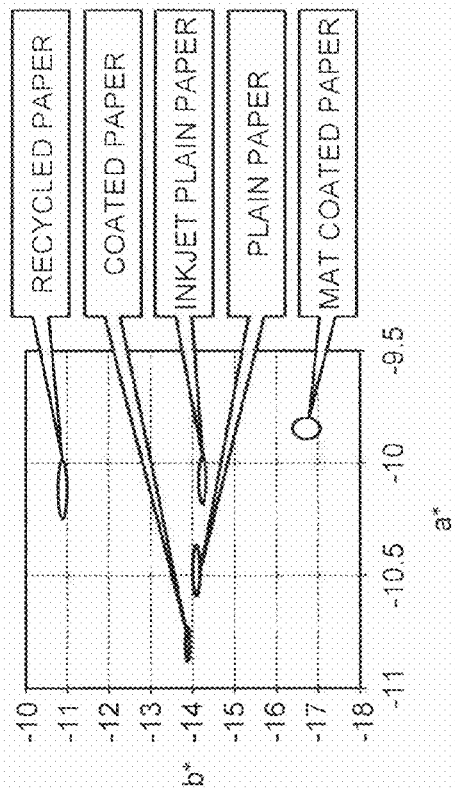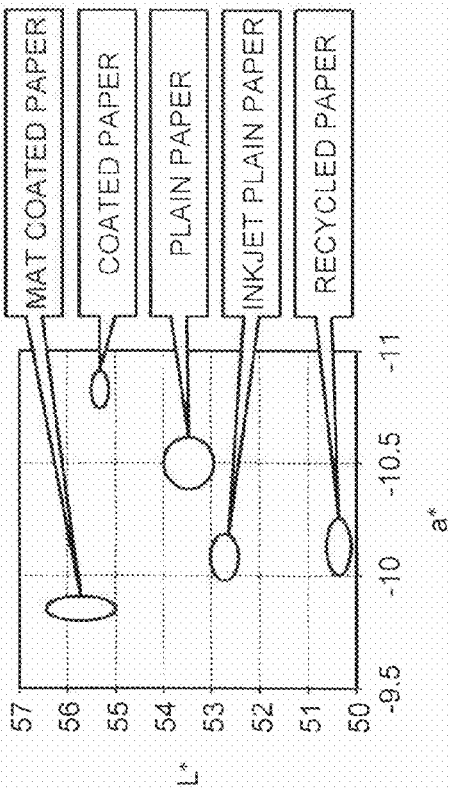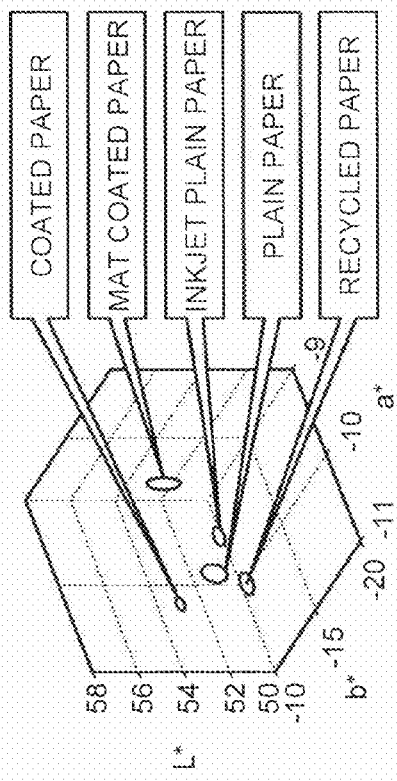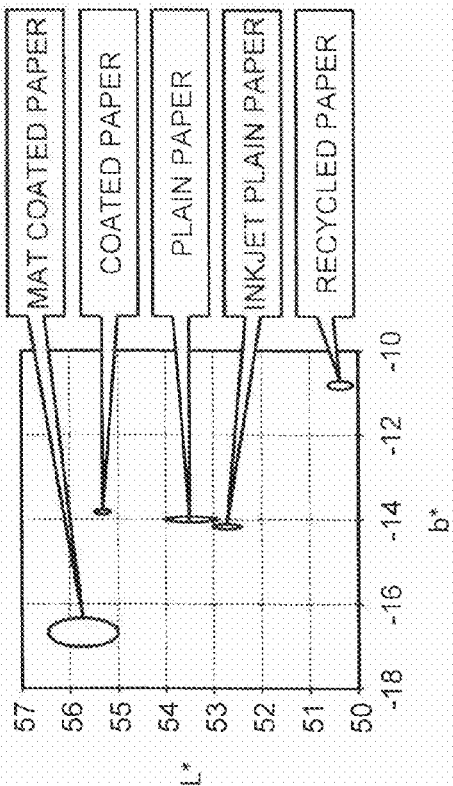

FIG.23

| TYPE OF RECORDING MEDIUM | SPECULAR REFLECTION HISTOGRAM DATA ANALYSIS | DIFFUSED REFLECTION HISTOGRAM DATA ANALYSIS | SPECULAR REFLECTION RESIDUAL HISTOGRAM DATA ANALYSIS | DIFFUSED REFLECTION RGB DATA ANALYSIS |
|---|---|---|---|---|
| PLAIN PAPER | C1 | B2 | B3 | A4 |
| RECYCLED PAPER | C1 | B2 | B3 | B4 |
| INKJET PLAIN PAPER | C1 | B2 | B3 | C4 |
| TRACING PAPER | B1 | A2 | - | - |
| MAT FILM | B1 | B2 | - | - |
| MAT COATED PAPER | C1 | B2 | B3 | D4 |
| COATED PAPER | C1 | B2 | B3 | E4 |
| GLOSSY PAPER | A1 | - | - | - |
| SEMI-GLOSSY PAPER | C1 | B2 | A3 | - |

FIG.24

| TYPE OF RECORDING MEDIUM | SPECULAR REFLECTION HISTOGRAM DATA ANALYSIS | DIFFUSED REFLECTION HISTOGRAM DATA ANALYSIS | SPECULAR REFLECTION RESIDUAL HISTOGRAM DATA ANALYSIS | DIFFUSED REFLECTION RGB DATA ANALYSIS |
|---|---|---|---|---|
| PLAIN PAPER | B1 | C2 | B3 | A4 |
| RECYCLED PAPER | B1 | C2 | B3 | B4 |
| INKJET PLAIN PAPER | B1 | C2 | B3 | C4 |
| TRACING PAPER | B1 | B2 | A3 | - |
| MAT FILM | B1 | B2 | B3 | - |
| MAT COATED PAPER | B1 | C2 | B3 | D4 |
| COATED PAPER | B1 | C2 | B3 | E4 |
| GLOSSY PAPER | A1 | A2 | - | - |
| SEMI-GLOSSY PAPER | A1 | C2 | - | - |

FIG.25

| TYPE OF RECORDING MEDIUM/ PRINTING MODE | FAST (LINE DRAWING) | FAST | STANDARD | HIGH QUALITY |
|---|---|---|---|---|
| PLAIN PAPER | A | B | B | B |
| RECYCLED PAPER | A | B | B | B |
| INKJET PLAIN PAPER | A | B | B | B |
| TRACING PAPER | - | B | B | B |
| MAT FILM | - | - | B | C |
| MAT COATED PAPER | A | C | B | D |
| COATED PAPER | - | C | B | D |
| GLOSSY PAPER | - | - | - | E |
| SEMI-GLOSSY PAPER | - | C | B | E |

FIG.26

| PRINTING TYPE | DISCHARGING TYPE | RESOLUTION |
|---|---|---|
| A | LARGE DROPLET | 600 dpi |
| B | MIDDLE DROPLET | 600 dpi |
| C | SMALL DROPLET | 600 dpi |
| D | MIDDLE DROPLET | 1200 dpi |
| E | SMALL DROPLET | 1200 dpi |

FIG.27

| TYPE OF RECORDING MEDIUM | PRINTING MODE |
|---|---|
| PLAIN PAPER | FAST |
| RECYCLED PAPER | FAST |
| INKJET PLAIN PAPER | FAST |
| TRACING PAPER | STANDARD |
| MAT FILM | HIGH QUALITY |
| MAT COATED PAPER | STANDARD |
| COATED PAPER | STANDARD |
| GLOSSY PAPER | HIGH QUALITY |
| SEMI-GLOSSY PAPER | HIGH QUALITY |

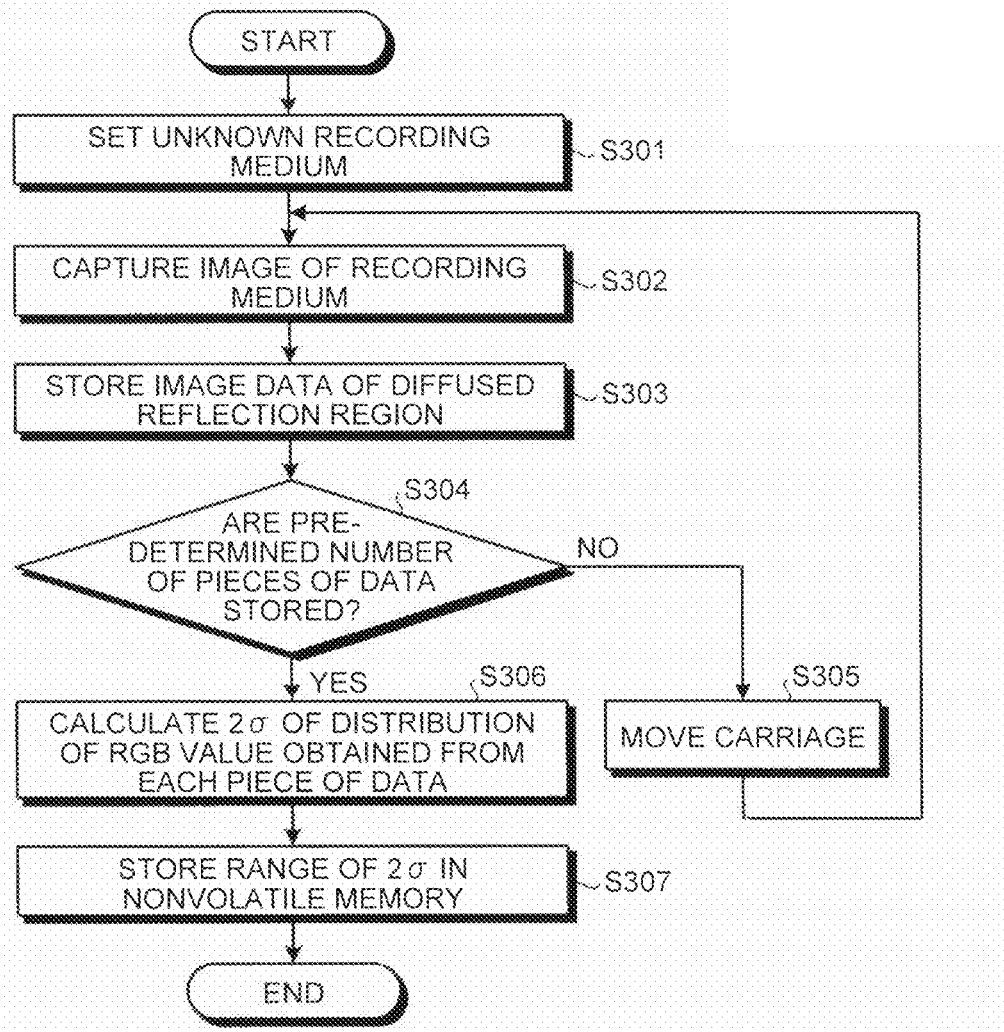

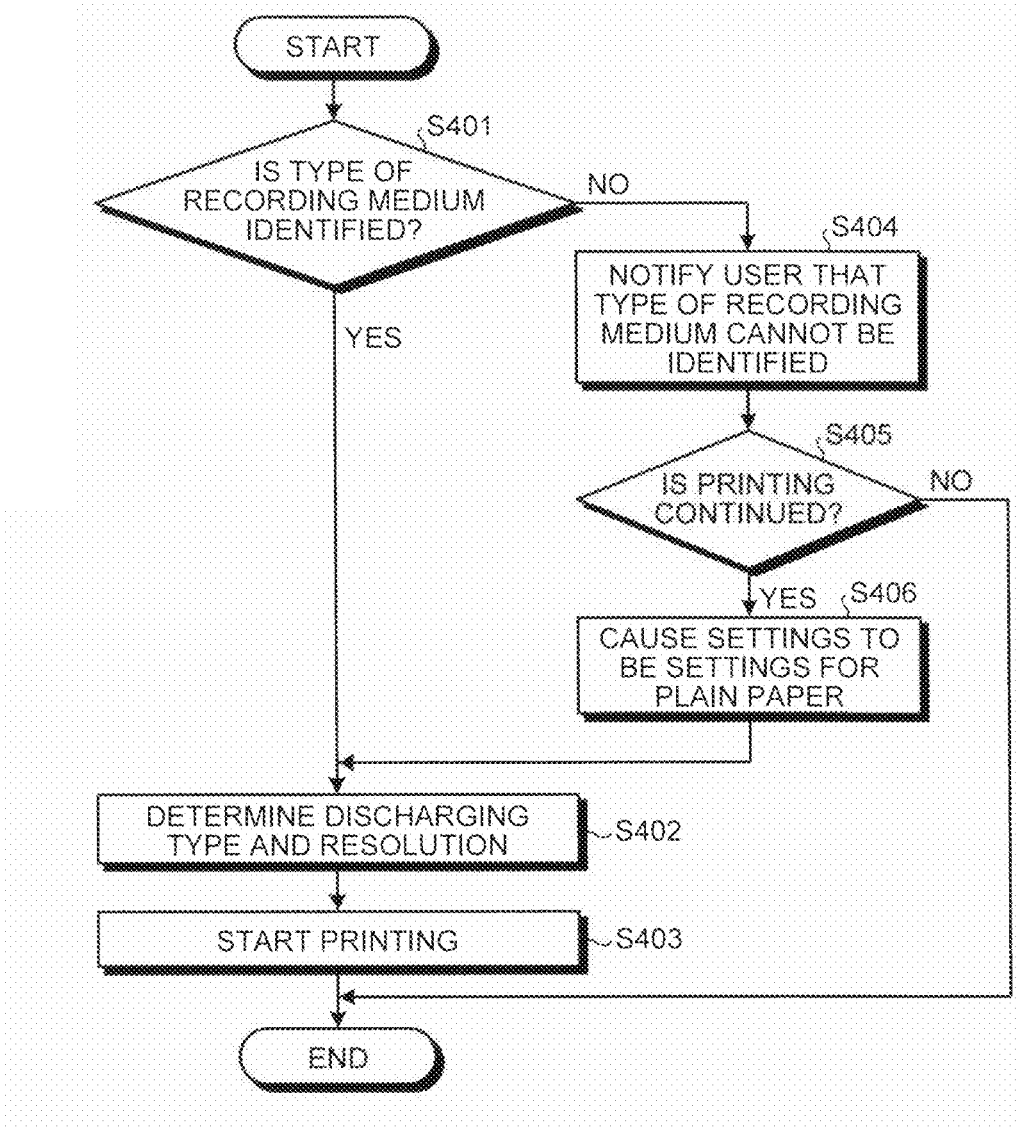

MEDIUM IDENTIFICATION DEVICE, IMAGE FORMING APPARATUS, METHOD OF IDENTIFYING MEDIUM, AND COMPUTER PROGRAM PRODUCT

CROSS-REFERENCE TO RELATED APPLICATIONS

The present application claims priority to and incorporates by reference the entire contents of Japanese Patent Application No. 2014-158015 filed in Japan on Aug. 1, 2014.

BACKGROUND OF THE INVENTION

1. Field of the Invention

The present invention relates to a medium identification device, an image forming apparatus, a method of identifying a medium, and a computer program product.

2. Description of the Related Art

Regarding an image forming apparatus that forms an image on a recording medium, known is a technique for automatically identifying a type of a recording medium to be used and changing a condition for an image forming process according to the identified type of the recording medium to perform optimum image formation on the recording medium to be used.

For example, Japanese Patent Application Laid-open No. 2002-182518 and Japanese Patent Application Laid-open No. 2003-302885 disclose an image forming apparatus that identifies a type of a recording medium using a method of detecting surface smoothness of the recording medium by using an image of the recording medium captured with a CMOS sensor, and variably controls a developing condition, a transferring condition, or a fixing condition. Japanese Patent Application Laid-open No. 2007-55814 discloses an example for identifying the type of the recording medium, in which surface smoothness and reflectivity of the recording medium is obtained by detecting reflected light from the recording medium with a CMOS sensor, and a thickness of the recording medium is obtained by detecting transmitted light that transmits through the recording medium with the CMOS sensor.

However, types of recording media that can be used for image formation have been increasing in recent years, and there are many types that cannot be identified according to the related art. Thus, desired is a novel technique for identifying more variety of recording media.

SUMMARY OF THE INVENTION

It is an object of the present invention to at least partially solve the problems in the conventional technology.

A medium identification device identifies a type of a recording medium used for image formation. The medium identification device includes: a two-dimensional image sensor that captures an image of the recording medium; and an identifying unit that obtains a glossiness evaluation value indicating glossiness of the recording medium, a surface roughness evaluation value indicating surface roughness of the recording medium, and a coloring evaluation value indicating coloring of the recording medium, using image data of a specular reflection region reflecting specular reflection light from the recording medium and image data of a diffused reflection region reflecting diffused reflection light from the recording medium, the regions being in the image of the recording medium, and identifies the type of the recording medium by combining determination using the glossiness evaluation value, determination using the surface roughness evaluation value, and determination using the coloring evaluation value.

A method of identifying a medium is executed by a medium identification device that comprises a two-dimensional image sensor. The method includes: capturing an image of a recording medium with the two-dimensional image sensor; and obtaining a glossiness evaluation value indicating glossiness of the recording medium, a surface roughness evaluation value indicating surface roughness of the recording medium, and a coloring evaluation value indicating coloring of the recording medium, using image data of a specular reflection region reflecting specular reflection light from the recording medium and image data of a diffused reflection region reflecting diffused reflection light from the recording medium, the regions being in the image of the recording medium, and identifying a type of the recording medium by combining determination using the glossiness evaluation value, determination using the surface roughness evaluation value, and determination using the coloring evaluation value.

A computer program product includes a non-transitory computer-readable medium containing an information processing program. The program causes a computer of a medium identification device that comprises a two-dimensional image sensor, to implement: a function of capturing an image of a recording medium with the two-dimensional image sensor; and a function of obtaining a glossiness evaluation value indicating glossiness of the recording medium, a surface roughness evaluation value indicating surface roughness of the recording medium, and a coloring evaluation value indicating coloring of the recording medium, using image data of a specular reflection region reflecting specular reflection light from the recording medium and image data of a diffused reflection region reflecting diffused reflection light from the recording medium, the regions being in the image of the recording medium, and identifying a type of the recording medium by combining determination using the glossiness evaluation value, determination using the surface roughness evaluation value, and determination using the coloring evaluation value.

The above and other objects, features, advantages and technical and industrial significance of this invention will be better understood by reading the following detailed description of presently preferred embodiments of the invention, when considered in connection with the accompanying drawings.

BRIEF DESCRIPTION OF THE DRAWINGS

FIG. 1 is a perspective view illustrating the inside of an image forming apparatus being seen through;

FIG. 5 is a block diagram illustrating a schematic configuration of a control mechanism of the image forming apparatus;

FIG. 6 is a block diagram illustrating a configuration example of a control mechanism of the colorimetric camera;

FIG. 7 is a flowchart illustrating an operation procedure of the colorimetric camera in identifying a medium;

FIGS. 21A to 21D is a diagram illustrating a coordinate range in an L*a*b* color space that is set for each type of the registered recording medium;

FIG. 23 is a diagram for explaining a relation between an example of the processing procedure performed by the identifying unit and identification results;

FIG. 24 is a diagram for explaining a relation between another example of the processing procedure performed by the identifying unit and identification results;

FIG. 25 is a diagram illustrating a relation between an optimum printing type, and the types of the recording media and printing modes;

FIG. 26 is a diagram illustrating a discharging type and resolution corresponding to each printing type;

FIG. 27 is a diagram illustrating a relation between the types of the recording media and the printing mode that is automatically set;

FIG. 28 is a flowchart illustrating an example of processing of generating and storing information for identifying a type of an unknown recording medium;

FIG. 29 is a flowchart illustrating an operation of the image forming apparatus after the processing of identifying the type of the recording medium is ended;

DETAILED DESCRIPTION OF THE PREFERRED EMBODIMENTS

The following describes an embodiment of a medium identification device, an image forming apparatus, a method of identifying a medium, and a computer program product in detail with reference to the attached drawings. The following embodiment describes an example of causing a colorimetric camera to have a function as a medium identification device according to the present invention, the colorimetric camera being mounted on an image forming apparatus constructed as an inkjet printer and having a function of capturing an image of a colorimetric pattern formed on a recording medium by the image forming apparatus to calculate a colorimetric value.

Mechanical Configuration of Image Forming Apparatus

Figure 1:
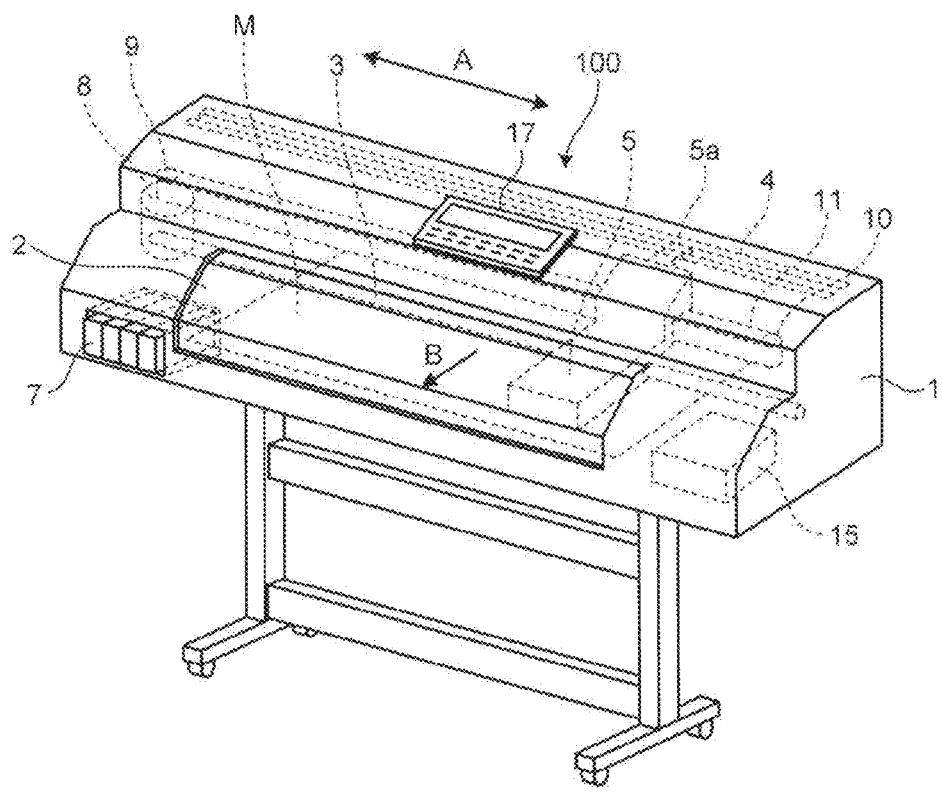
Figure 2:
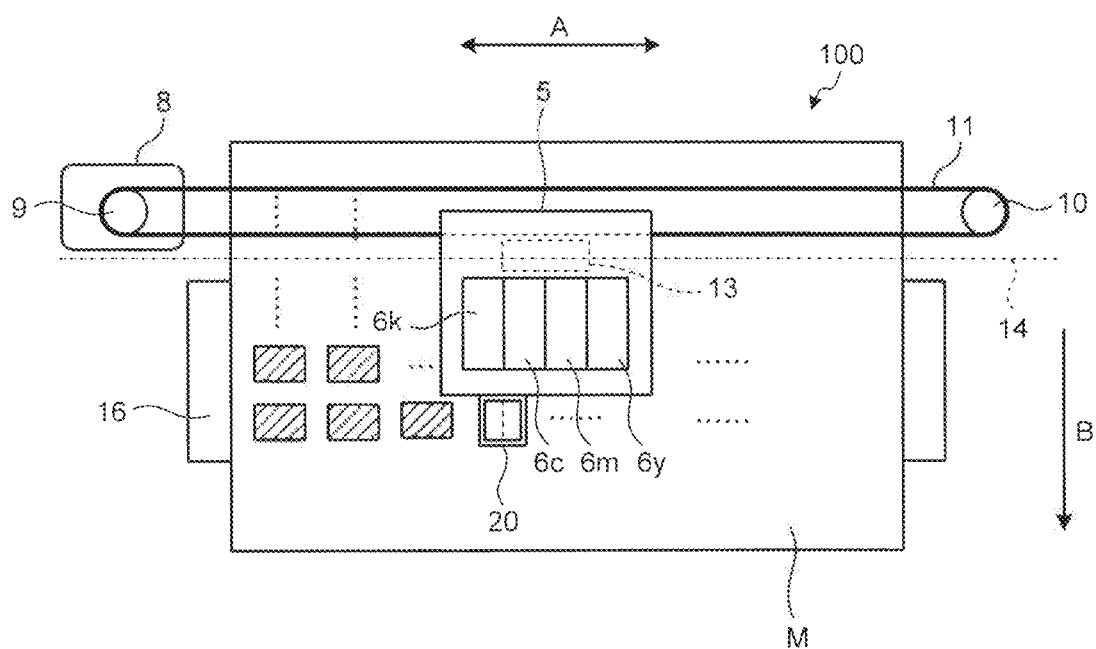
FIG. 2 is a top view illustrating a mechanical configuration of the inside of the image forming apparatus.
Figure 3:
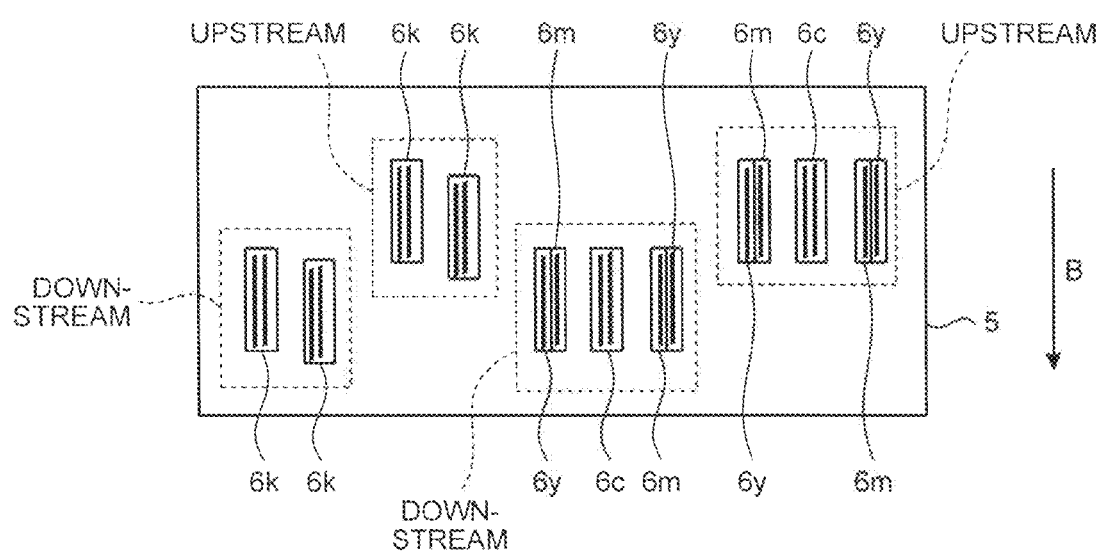
FIG. 3 is a diagram for explaining an arrangement example of recording heads mounted on a carriage.

First, the following describes a mechanical configuration of an image forming apparatus 100 according to the embodiment with reference to FIGS. 1 to 3. FIG. 1 is a perspective view illustrating the inside of the image forming apparatus 100 being seen through. FIG. 2 is a top view illustrating a mechanical configuration of the inside of the image forming apparatus 100. FIG. 3 is a diagram for explaining an arrangement example of recording heads 6 mounted on a carriage 5.

As illustrated in FIG. 1, the image forming apparatus 100 according to the embodiment includes the carriage 5 that reciprocates in a main scanning direction (the arrow A direction in FIG. 1). The carriage 5 is supported by a main guide rod 3 extended along the main scanning direction. A connecting piece 5a is provided to the carriage 5. The connecting piece 5a is engaged with a sub-guide member 4 arranged in parallel with the main guide rod 3 and stabilizes a posture of the carriage 5.

As illustrated in FIG. 2, the carriage 5 includes a recording head 6y that discharges yellow ink, a recording head 6m that discharges magenta ink, a recording head 6c that discharges cyan ink, and a recording head 6k that discharges black ink (hereinafter, when the recording heads 6y, 6m, 6c, and 6k are collectively referred to, they are referred to as a "recording head 6") mounted thereon. The recording head 6 is mounted on the carriage 5 so that a discharge face (nozzle face) thereof faces downward (toward a recording medium M).

A cartridge 7 serving as an ink supplier for supplying ink to the recording head 6 is not mounted on the carriage 5, and arranged at a predetermined position in the image forming apparatus 100. The cartridge 7 is coupled to the recording head 6 with a pipe (not illustrated), and ink is supplied from the cartridge 7 to the recording head 6 through the pipe.

The carriage 5 is coupled to a timing belt 11 stretched between a driving pulley 9 and a driven pulley 10. The driving pulley 9 is rotated by driving of the main scanning motor 8. The driven pulley 10 has a mechanism that adjusts a distance between the driven pulley 10 and the driving pulley 9, and serves to give predetermined tension to the timing belt 11. The carriage 5 reciprocates in the main scanning direction when the timing belt 11 is fed by the driving of the main scanning motor 8. For example, as illustrated in FIG. 2, the movement of the carriage 5 in the main scanning direction is controlled based on an encoder value obtained by detecting a mark on an encoder sheet 14 by an encoder sensor 13 arranged on the carriage 5.

The image forming apparatus 100 according to the embodiment includes a maintenance mechanism 15 for maintaining reliability of the recording head 6. The maintenance mechanism 15 cleans or caps the discharge face of the recording head 6, and causes unnecessary ink to be ejected from the recording head 6.

As illustrated in FIG. 2, a platen 16 is arranged at a position opposite to the discharge face of the recording head 6. The platen 16 supports the recording medium M when ink is discharged from the recording head 6 onto the recording medium M. The image forming apparatus 100 according to the embodiment is a wide machine in which a moving distance of the carriage 5 in the main scanning direction is long. Thus, the platen 16 is configured by connecting a plurality of plate members in the main scanning direction (moving direction of the carriage 5). The recording medium M is held by conveyance rollers driven by a sub-scanning motor (not illustrated) to be intermittently conveyed in a sub-scanning direction (the arrow B direction in FIG. 2) on the platen 16.

The recording head 6 includes a plurality of nozzle arrays, and causes the nozzle arrays to discharge ink onto the recording medium M conveyed on the platen 16 to form an image on the recording medium M. In the embodiment, to secure a large width of the image that can be formed on the recording medium M through one scanning process performed by the carriage 5, as illustrated in FIG. 3, the carriage 5 includes the upstream recording head 6 and the downstream recording head 6 mounted thereon. The number of recording heads 6$k$ that is mounted on the carriage 5 and discharges black ink is two times the number of recording heads 6$y$, 6$m$, and 6$c$ that discharge color ink. The recording heads 6$y$ and 6$m$ are arranged separately on the left and the right. This arrangement causes overlapping orders of colors in the outward operation and the return operation of the carriage 5 to be identical to each other, and prevents the colors from being changed between an outward route and a return route. The arrangement of the recording heads 6 illustrated in FIG. 3 is merely an example, and the embodiment is not limited thereto.

The components constituting the image forming apparatus 100 according to the embodiment are arranged inside an exterior body 1. A covering member 2 is provided to the exterior body 1 in an openable manner. When maintenance of the image forming apparatus 100 is performed or a paper jam occurs, work can be conducted for the components arranged inside the exterior body 1 by opening the covering member 2.

The image forming apparatus 100 according to the embodiment includes an operation panel 17 that displays various pieces of information and receives an operation from a user. The operation panel 17 is connected to a main control board (described later) arranged inside the exterior body 1 via a connecting cable (not illustrated).

The image forming apparatus 100 according to the embodiment intermittently conveys the recording medium M in the sub-scanning direction on the platen 16, moves the carriage 5 in the main scanning direction while the conveyance of the recording medium M in the sub-scanning direction is stopped, and causes the nozzle arrays of the recording head 6 mounted on the carriage 5 to discharge ink onto the recording medium M on the platen 16 to form an image on the recording medium M.

Specifically, when color adjustment is performed in the image forming apparatus 100, ink is discharged from the nozzle arrays of the recording head 6 mounted on the carriage 5 onto the recording medium M on the platen 16 to form a large number of calorimetric patterns, and colorimetry is performed on the colorimetric patterns. The calorimetric pattern is formed on the recording medium M by the image forming apparatus 100 actually using the ink, and reflects a characteristic specific to the image forming apparatus 100. Accordingly, a device profile describing the characteristic specific to the image forming apparatus 100 can be generated or modified using colorimetric values of the large number of calorimetric patterns. By performing color conversion between a standard color space and a device-dependent color based on the device profile, the image forming apparatus 100 can output an image with high reproducibility.

The image forming apparatus 100 according to the embodiment includes a colorimetric camera 20 having a function of capturing the image of the colorimetric pattern formed on the recording medium M and calculating the colorimetric value. As illustrated in FIG. 2, the colorimetric camera 20 is supported by the carriage 5 on which the recording head 6 is mounted. The colorimetric camera 20 moves over the recording medium M on which the colorimetric pattern is formed due to the conveyance of the recording medium M and the movement of the carriage 5. When reaching a position opposite to the calorimetric pattern, the calorimetric camera 20 captures the image. The colorimetric value of the colorimetric pattern is then calculated based on an RGB value of the colorimetric pattern obtained through the image capturing process.

The colorimetric camera 20 also has a function of identifying the type of the recording medium M to be used in image formation in addition to the function of calculating the colorimetric value of the colorimetric pattern. The image forming apparatus 100 according to the embodiment can perform optimum image formation on the recording medium M to be used, by determining, for example, a discharging type (a large droplet, a middle droplet, and a small droplet) of the ink discharged from the recording head 6 and resolution of the image to be formed on the recording medium M according to the type of the recording medium M identified by the colorimetric camera 20. A specific method of identifying the type of the recording medium M using the colorimetric camera 20 will be described later in detail.

Specific Example of Colorimetric Camera

Figure 4A:
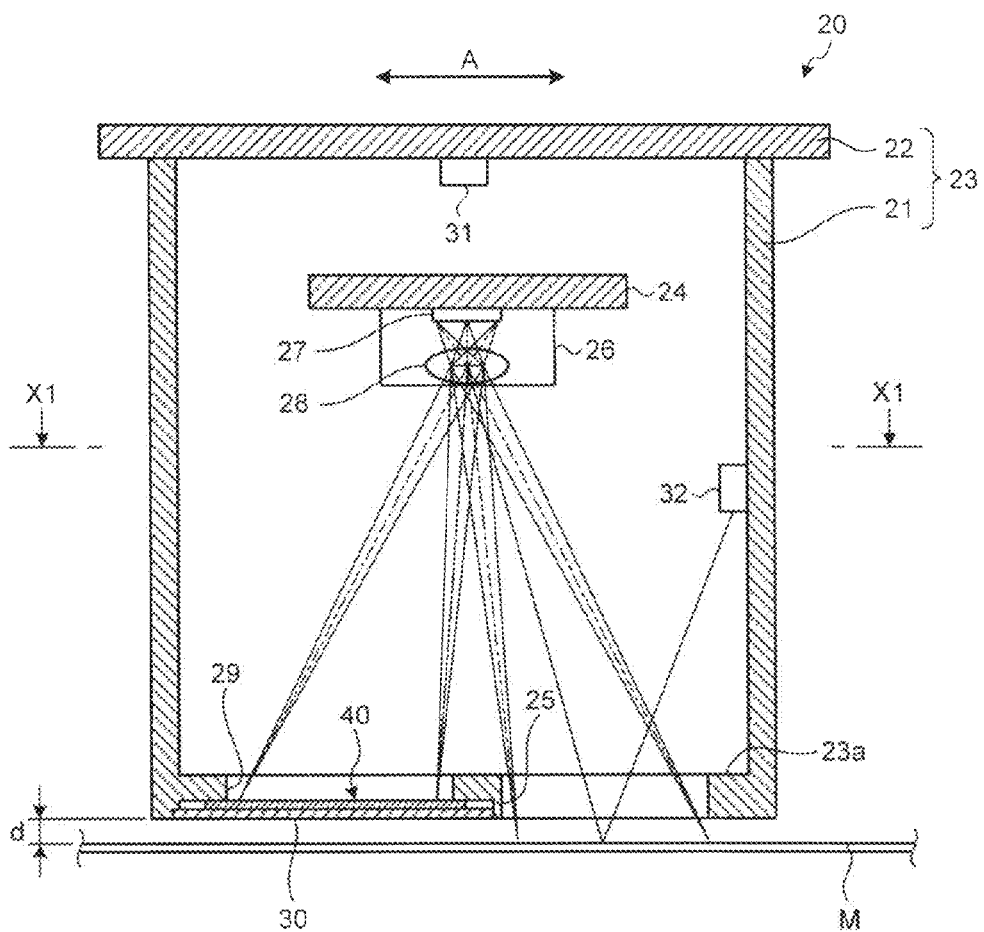
FIG. 4A is a vertical cross-sectional view of a colorimetric camera.
Figure 4B:
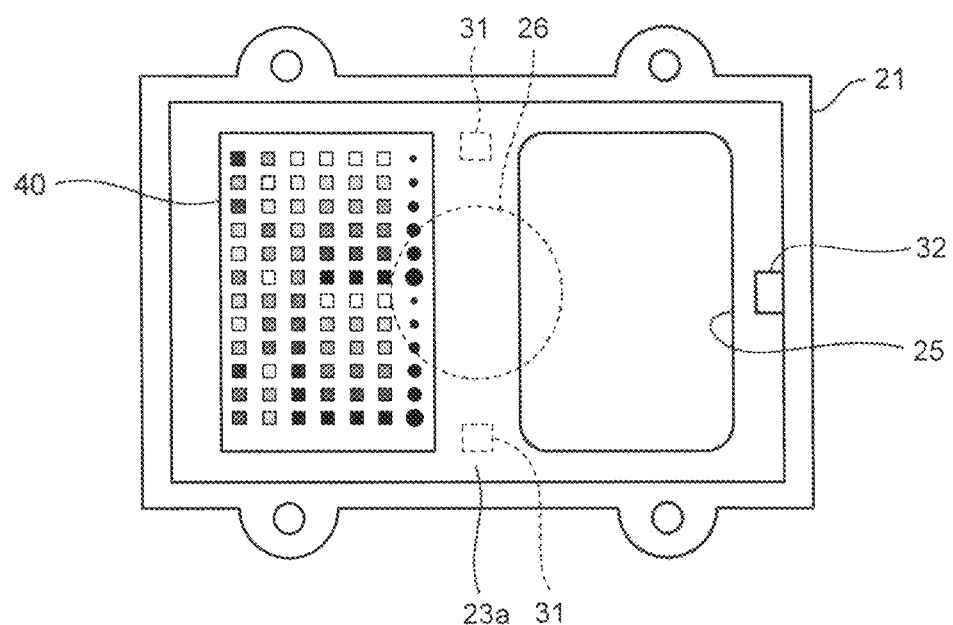
FIG. 4B is a plan view of a bottom face of a housing of the colorimetric camera viewed from the X1 direction in FIG. 4A.

Next, the following describes a specific example of the colorimetric camera 20 in detail with reference to FIGS. 4A and 4B. FIGS. 4A and 4B are diagrams illustrating a specific example of the colorimetric camera 20. FIG. 4A is a vertical cross-sectional view of the colorimetric camera 20, and FIG. 4B is a plan view of a bottom face 23$a$ of a housing 23 of the colorimetric camera 20 viewed from the X1 direction in FIG. 4A. In FIG. 4B, to clarify a positional relation between respective components arranged inside the colorimetric camera 20, positions where a two-dimensional image sensor 26 and a first light source 31 (both are described later) are projected onto the bottom face 23$a$ are indicated by dashed lines.

The colorimetric camera 20 includes the housing 23 constructed by combining a frame body 21 and a substrate 22. The frame body 21 is formed in a bottomed cylindrical shape which is opened at one end being an upper surface of the housing 23. The substrate 22 is fastened to the frame body 21 with a fastening member and integrated with the frame body 21 to close an open end of the frame body 21 and forms the upper surface of the housing 23.

The housing 23 is fixed to the carriage 5 so that the bottom face 23$a$ thereof is opposite to the recording medium M on the platen 16 with a predetermined gap d therebetween. An opening 25 is provided to the bottom face 23$a$ of the housing 23 opposite to the recording medium M so that an image of the recording medium M (the calorimetric pattern when the color adjustment is performed) can be captured from the inside of the housing 23.

The two-dimensional image sensor 26 for capturing the image is arranged inside the housing 23. The two-dimensional image sensor 26 includes a sensor chip 27 such as a CCD image capturing device or a CMOS image capturing device, and an imaging forming lens 28 that forms an optical image in an image capturing area of the two-dimensional image sensor 26 on a sensor face of the sensor chip 27. The sensor chip 27 is mounted, for example, on a sensor substrate 24 supported by a supporting member (not illustrated) so that the sensor face thereof faces the bottom face 23a of the housing 23. The imaging forming lens 28 is fixed to the sensor chip 27 in a positioned state to keep a positional relation that is determined according to optical characteristics of the imaging forming lens 28.

Another opening 29 is provided to the bottom face 23a of the housing 23, the opening 29 being adjacent to the opening 25 through which the two-dimensional image sensor 26 captures an image of a subject outside the housing 23. A reference chart 40 is arranged to close the opening 29 from the outside of the housing 23, and held by a holding member 30. The holding member 30 is attached to the housing 23 in a detachable manner. Accordingly, the reference chart 40 can be replaced by detaching the holding member 30 from the housing 23. An image of the reference chart 40 is captured by the two-dimensional image sensor 26 together with the colorimetric pattern to obtain a correct colorimetric value of the colorimetric pattern.

The first light source 31 and a second light source 32 are arranged inside the housing 23 as light sources for illuminating the image capturing area of the two-dimensional image sensor 26.

The first light source 31 is a light source that illuminates the image capturing area of the two-dimensional image sensor 26 almost uniformly with diffused light, and is arranged so that specular reflection light from the recording medium M outside the housing 23 and specular reflection light from the reference chart 40 inside the housing 23 are not incident on the two-dimensional image sensor 26. In the embodiment, a light emitting diode (LED) mounted on an inner face of the substrate 22 is used as the first light source 31. The first light source 31 is not necessarily mounted on the substrate 22 directly. The first light source 31 may be arranged at a position where the specular reflection light from the recording medium M or the reference chart 40 can be prevented from being incident on the two-dimensional image sensor 26 and the image capturing area of the two-dimensional image sensor 26 can be almost uniformly illuminated. In the embodiment, the LED is used as the first light source 31, but the type of the light source is not limited to the LED. For example, organic EL or the like may be used as the first light source 31. When the organic EL is used as the first light source 31, illumination light close to a spectral distribution of sunlight can be obtained, so that improvement in colorimetric accuracy is expected.

The second light source 32 is arranged so that the specular reflection light from the recording medium M outside the housing 23 is incident on the two-dimensional image sensor 26. In the embodiment, an LED arranged on a side wall of the frame body 21 positioned close to the opening 25 is used as the second light source 32. The second light source 32 may be arranged so that the specular reflection light that is emitted from the second light source 32 and regularly reflected by the recording medium M outside the housing 23 is incident on the two-dimensional image sensor 26, and may be arranged at a position other than the side wall of the frame body 21. Similarly to the first light source 31, a light source other than the LED may be used as the second light source 32.

In identifying the type of the recording medium M (hereinafter, referred to as "in identifying the medium"), the colorimetric camera 20 according to the embodiment uses image data of a specular reflection region that is a region in the image of the recording medium M captured by the two-dimensional image sensor 26 and reflects the specular reflection light from the recording medium M, and image data of a diffused reflection region that reflects diffused reflection light from the recording medium M. The image data of the specular reflection region can be acquired from the image of the recording medium M captured by the two-dimensional image sensor 26 under illumination of the second light source 32. The image data of the diffused reflection region may be acquired from the image of the recording medium M captured by the two-dimensional image sensor 26 under illumination of the second light source 32, or acquired from the image of the recording medium M captured by the two-dimensional image sensor 26 under illumination of the first light source 31.

The mechanical configuration of the calorimetric camera 20 described above is merely an example, and the configuration is not limited thereto. It is sufficient that the colorimetric camera 20 according to the embodiment can at least perform colorimetry on the colorimetric pattern or identify the type of the recording medium M using the image captured by the two-dimensional image sensor 26, and the configuration described above can be variously changed or modified. Modifications of the colorimetric camera 20 will be described later in detail.

In the embodiment, the colorimetric camera 20 having a function of performing colorimetry on the colorimetric pattern is made to have a function as a medium identification device that identifies the type of the recording medium M. Alternatively, the medium identification device may be implemented using an image capturing device other than the colorimetric camera 20.

Schematic Configuration of Control Mechanism of Image Forming Apparatus

Next, the following describes a schematic configuration of a control mechanism of the image forming apparatus 100 according to the embodiment with reference to FIG. 5. FIG. 5 is a block diagram illustrating the schematic configuration of the control mechanism of the image forming apparatus 100.

The image forming apparatus 100 according to the embodiment includes, as illustrated in FIG. 5, a CPU 101, a ROM 102, a RAM 103, a recording head driver 104, a main scanning driver 105, a sub-scanning driver 106, a field-programmable gate array (FPGA) for control 110, the recording head 6, the colorimetric camera 20, the encoder sensor 13, the main scanning motor 8, a sub-scanning motor 12, and the operation panel 17. The CPU 101, the ROM 102, the RAM 103, the recording head driver 104, the main scanning driver 105, the sub-scanning driver 106, and the FPGA for control 110 are mounted on a main control board 120. The recording head 6, the encoder sensor 13, and the colorimetric camera 20 are mounted on the carriage 5 as described above.

The CPU 101 serves to totally control the image forming apparatus 100. For example, the CPU 101 executes various control programs stored in the ROM 102 utilizing the RAM 103 as a working area, and outputs a control command for controlling various operations in the image forming apparatus 100.

The recording head driver 104, the main scanning driver 105, and the sub-scanning driver 106 are drivers for driving the recording head 6, the main scanning motor 8, and the sub-scanning motor 12, respectively.

The FPGA for control 110 controls various operations in the image forming apparatus 100 in cooperation with the CPU 101. The FPGA for control 110 includes, for example, a CPU control unit 111, a memory control unit 112, an ink discharge control unit 113, a sensor control unit 114, a motor control unit 115, and a notification unit 116 as functional components.

The CPU control unit 111 communicates with the CPU 101 to transmit various pieces of information acquired by the FPGA for control 110 to the CPU 101, and inputs the control command output from the CPU 101.

The memory control unit 112 performs memory control so that the CPU 101 accesses the ROM 102 and the RAM 103.

The ink discharge control unit 113 controls the operation of the recording head driver 104 according to the control command from the CPU 101 to control the operation of the recording head 6 driven by the recording head driver 104. In particular, according to the embodiment, the ink discharge control unit 113 determines the discharging type of the ink (a large droplet, a middle droplet, and a small droplet) discharged from the recording head 6 to the recording medium M and the resolution of the image to be formed on the recording medium M according to the type of the recording medium M identified by the colorimetric camera 20, and controls the operation of the recording head 6 to perform image formation on the recording medium M with the determined discharging type and resolution.

The sensor control unit 114 performs processing on a sensor signal such as an encoder value output from the encoder sensor 13.

The motor control unit 115 controls the operation of the main scanning driver 105 according to the control command from the CPU 101 to control the main scanning motor 8 driven by the main scanning driver 105, and controls movement of the carriage 5 in the main scanning direction. The motor control unit 115 also controls the operation of the sub-scanning driver 106 according to the control command from the CPU 101 to control the sub-scanning motor 12 driven by the sub-scanning driver 106, and controls movement of the recording medium M on the platen 16 in the sub-scanning direction.

The notification unit 116 causes, for example, the operation panel 17 to display a predetermined message when the colorimetric camera 20 cannot identify the type of the recording medium M, and notifies a user using the image forming apparatus 100 that the type of the recording medium M cannot be identified. A method of notification to the user is not limited to display of the message by the operation panel 17. For example, a method of sounding a buzzer (not illustrated) may be used.

The components described above are merely an example of control functions implemented by the FPGA for control 110. Various control functions other than the above components may be implemented by the FPGA for control 110. All or some of the control functions may be implemented by a computer program executed by the CPU 101 or another general-purpose CPU. Some of the control functions may be implemented by dedicated hardware such as another FPGA different from the FPGA for control 110 or an application specific integrated circuit (ASIC).

The recording head 6 is driven by the recording head driver 104 the operation of which is controlled by the CPU 101 and the FPGA for control 110, and discharges the ink onto the recording medium M on the platen 16 to form the image.

As described above, the colorimetric camera 20 captures, with the two-dimensional image sensor 26, an image of the colorimetric pattern formed on the recording medium M under the illumination of the first light source 31 when color adjustment is performed in the image forming apparatus 100 together with an image of the reference chart 40, and calculates the colorimetric value of the colorimetric pattern (a color specification value in a standard color space, for example, an L*a*b* value in an L*a*b* color space) based on the RGB value of the colorimetric pattern obtained from the captured image and the RGB value of each reference patch in the reference chart 40. The colorimetric value of the colorimetric pattern calculated by the colorimetric camera 20 is transmitted to the CPU 101 via the FPGA for control 110. As a specific method of calculating the colorimetric value of the colorimetric pattern, a method disclosed in Japanese Patent Application Laid-open No. 2013-051671 can be used, for example.

As described above, the colorimetric camera 20 captures, with the two-dimensional image sensor 26, the image of the recording medium M before the image is formed (before the colorimetric pattern is formed when color adjustment is performed), and acquires image data of the specular reflection region and image data of the diffused reflection region. Then, the colorimetric camera 20 uses the image data of the specular reflection region and the image data of the diffused reflection region to identify the type of the recording medium M to be used for image formation using a method described later. In the embodiment, it is assumed that the image data of the diffused reflection region is acquired from the image of the recording medium M captured by the two-dimensional image sensor 26 under the illumination of the first light source 31, and the image data of the specular reflection region is acquired from the image of the recording medium M captured by the two-dimensional image sensor 26 under the illumination of the second light source 32. That is, the two-dimensional image sensor 26 captures an image two times to acquire the image data of the specular reflection region of the recording medium M and the image data of the diffused reflection region thereof. Alternatively, both of the image data of the specular reflection region and the image data of the diffused reflection region may be acquired from the image of the recording medium M captured by the two-dimensional image sensor 26 under the illumination of the second light source 32. Medium information indicating the type of the recording medium M identified by the colorimetric camera 20 is transmitted to the ink discharge control unit 113 in the FPGA for control 110. When the type of the recording medium M cannot be identified, the medium information indicating that fact is transmitted from the colorimetric camera 20 to the notification unit 116 in the FPGA for control 110.

The encoder sensor 13 outputs the encoder value obtained by detecting the mark on the encoder sheet 14 to the FPGA for control 110. The encoder value is transmitted from the FPGA for control 110 to the CPU 101 and is used for calculating a position or speed of the carriage 5, for example. The CPU 101 generates and outputs a control command for controlling the main scanning motor 8 based on the position or the speed of the carriage 5 calculated from the encoder value.

Configuration of Control Mechanism of Colorimetric Camera

Next, the following specifically describes a control mechanism of the colorimetric camera 20 with reference to FIG. 6. FIG. 6 is a block diagram illustrating a configuration example of the control mechanism of the colorimetric camera 20.

As illustrated in FIG. 6, the colorimetric camera 20 includes a timing signal generating unit 41, a frame memory 42, an averaging processing unit 43, a colorimetric operation unit 44, a nonvolatile memory 45, a light source driving control unit 46, and an identifying unit 47 in addition to the two-dimensional image sensor 26, the first light source 31, and the second light source 32 described above.

The two-dimensional image sensor 26 converts the light incident on the two-dimensional image sensor 26 into an electric signal, and outputs image data obtained by capturing an image of the image capturing area. The two-dimensional image sensor 26 incorporates a function of AD converting an analog signal obtained through photoelectric conversion into digital image data, and performing various pieces of image processing such as shading correction, white balance correction, γ correction, and format conversion on the image data to be output. Settings of various operation conditions for the two-dimensional image sensor 26 are performed according to various setting signals from the CPU 101. Some or all of the various pieces of image processing on the image data may be performed outside the two-dimensional image sensor 26.

The timing signal generating unit 41 generates a timing signal for controlling a timing for capturing an image with the two-dimensional image sensor 26, and supplies the timing signal to the two-dimensional image sensor 26. According to the embodiment, the two-dimensional image sensor 26 captures an image not only in a case of performing colorimetry on the colorimetric pattern but also in a case of identifying the type of the recording medium M used for image formation. The timing signal generating unit 41 generates the timing signal for controlling the timing for starting capturing an image when the two-dimensional image sensor 26 captures the image, and supplies the timing signal to the two-dimensional image sensor 26.

The frame memory 42 temporarily stores the image output from the two-dimensional image sensor 26.

In performing colorimetry on the colorimetric pattern, the averaging processing unit 43 extracts a colorimetric target region set near the center portion of a region reflecting the colorimetric pattern and a region reflecting each reference patch of the reference chart 40 from the image that is output from the two-dimensional image sensor 26 and temporarily stored in the frame memory 42. The averaging processing unit 43 averages image data of the extracted colorimetric target region, and outputs the obtained value to the colorimetric operation unit 44 as the RGB value of the colorimetric pattern. The averaging processing unit 43 also averages image data of the region reflecting each reference patch, and outputs the obtained value to the colorimetric operation unit 44 as the RGB of each reference patch.

The colorimetric operation unit 44 calculates the colorimetric value of the colorimetric pattern based on the RGB value of the colorimetric pattern obtained through the processing performed by the averaging processing unit 43 and the RGB value of each reference patch of the reference chart 40. The colorimetric value of the colorimetric pattern calculated by the colorimetric operation unit 44 is transmitted to the CPU 101 on the main control board 120. The colorimetric operation unit 44 can calculate the colorimetric value of the colorimetric pattern using a method disclosed in Japanese Patent Application Laid-open No. 2013-051671, for example, so that processing performed by the colorimetric operation unit 44 will not be described in detail herein.

The nonvolatile memory 45 stores various pieces of data required for calculating the colorimetric value of the colorimetric pattern by the colorimetric operation unit 44, and various pieces of information referred to by the identifying unit 47 in identifying the medium.

The light source driving control unit 46 generates a light source driving signal for driving the first light source 31 or the second light source 32 to be supplied to the first light source 31 and the second light source 32. As described above, the colorimetric camera 20 according to the embodiment captures an image with the two-dimensional image sensor 26 under the illumination of the first light source 31 in performing colorimetry on the colorimetric pattern, and captures an image with the two-dimensional image sensor 26 under the illumination of the first light source 31 while capturing an image with the two-dimensional image sensor 26 under the illumination of the second light source 32 in identifying the medium. Accordingly, the light source driving control unit 46 supplies the light source driving signal to the first light source 31 in synchronization with a timing for capturing an image by the two-dimensional image sensor 26 in performing colorimetry on the calorimetric pattern, and sequentially supplies light source driving signals to the first light source 31 and the second light source 32 in synchronization with two timings for capturing an image by the two-dimensional image sensor 26 in identifying the medium.

The identifying unit 47 identifies the type of the recording medium M using the image of the recording medium M captured by the two-dimensional image sensor 26. Specifically, the identifying unit 47 first acquires, from the image of the recording medium M captured by the two-dimensional image sensor 26, the image data of the specular reflection region reflecting the specular reflection light from the recording medium M and the image data of the diffused reflection region reflecting the diffused reflection light from the recording medium M. The image data of the specular reflection region can be acquired by extracting the specular reflection region that is specified in accordance with a positional relation between the second light source 32 and the two-dimensional image sensor 26 from the image of the recording medium M captured by the two-dimensional image sensor 26 under the illumination of the second light source 32. The image data of the diffused reflection region can be acquired by extracting a predetermined region from the image of the recording medium M captured by the two-dimensional image sensor 26 under the illumination of the first light source 31. The image data of the diffused reflection region may be acquired by extracting an arbitrary region other than the specular reflection region from the image of the recording medium M captured by the two-dimensional image sensor 26 under the illumination of the second light source 32.

The identifying unit 47 obtains a glossiness evaluation value indicating glossiness of the recording medium M, a surface roughness evaluation value indicating surface roughness of the recording medium M, and a coloring evaluation value indicating coloring of the recording medium M using the image data of the specular reflection region and the image data of the diffused reflection region that are acquired as described above. The identifying unit 47 then identifies the type of the recording medium M by combining determination using the glossiness evaluation value, determination using the surface roughness evaluation value, and determination using the coloring evaluation value.

It is assumed that the identifying unit 47 according to the embodiment obtains, as the glossiness evaluation value, a peak value of a luminance histogram of the specular reflection region, and a value of a standard deviation σ of a histogram of a residual that is a difference between a luminance distribution in the specular reflection region and a normal distribution. In this case, the determination using the glossiness evaluation value includes processing of threshold determination of a peak value (a luminance value the frequency of which is the largest) of the luminance histogram of the specular reflection region, and processing of threshold comparison of the value of the standard deviation σ of the histogram of the residual that is a difference between the luminance distribution in the specular reflection region and the normal distribution. Hereinafter, the former processing is called "specular reflection histogram data analysis", and the latter processing is called "specular reflection residual histogram data analysis".

The identifying unit 47 according to the embodiment obtains, for example, the value of the standard deviation σ of the luminance histogram of the diffused reflection region as the surface roughness evaluation value. In this case, the determination using the surface roughness evaluation value is processing of threshold comparison of the value of the standard deviation σ of the luminance histogram of the diffused reflection region. Hereinafter, the above processing is called "diffused reflection histogram data analysis".

The identifying unit 47 according to the embodiment obtains, for example, a coordinate value of when the RGB value of the pixel included in the diffused reflection region is plotted in an RGB color space as the coloring evaluation value. In this case, the determination using the coloring evaluation value is processing of collating the coordinate value of when the RGB value of the pixel included in the diffused reflection region is plotted in the RGB color space with a coordinate range in the RGB color space set for each type of the registered recording medium M. Hereinafter, the above processing is called "diffused reflection RGB data analysis".

The identifying unit 47 according to the embodiment identifies the type of the recording medium M used for image formation by combining the "specular reflection histogram data analysis", the "specular reflection residual histogram data analysis", the "diffused reflection histogram data analysis", and the "diffused reflection RGB data analysis" described above. The following describes a specific example of processing performed by the identifying unit 47 in detail exemplifying a case of identifying which one of nine types of recording media including "glossy paper", "plain paper", "mat coated paper", "semi-glossy paper", "coated paper", "tracing paper", a "mat film", "inkjet plain paper", and "recycled paper" is used as the recording medium M for image formation.

Overview of Operation of Colorimetric Camera in Identifying Medium

The following describes an overview of an operation of the colorimetric camera 20 in identifying the medium with reference to FIG. 7. FIG. 7 is a flowchart illustrating an operation procedure of the colorimetric camera 20 in identifying the medium.

In identifying the medium, first, the image of the recording medium M is captured by the two-dimensional image sensor 26 under the illumination of the second light source (Step S101). The image of the recording medium M captured by the two-dimensional image sensor 26 is stored in the frame memory 42. The identifying unit 47 then extracts a predetermined region from the image of the recording medium M stored in the frame memory 42 to acquire the image data of the specular reflection region (Step S102).

Next, the image of the recording medium M is captured by the two-dimensional image sensor 26 under the illumination of the first light source 31 (Step S103). The image of the recording medium M captured by the two-dimensional image sensor 26 is stored in the frame memory 42. The identifying unit 47 then extracts a predetermined region from the image of the recording medium M stored in the frame memory 42 to acquire the image data of the diffused reflection region (Step S104). The order of the image capturing at Step S101 and the image capturing at Step S103 may be reversed. The image data of the specular reflection region and the image data of the diffused reflection region may be acquired after the image capturing at Step S101 and the image capturing at Step S103 are sequentially performed.

Next, the identifying unit 47 performs processing of identifying the type of the recording medium M based on the image data of the specular reflection region acquired at Step S102 and the image data of the diffused reflection region acquired at Step S104 (Step S105). The processing at Step S105 is processing combining the "specular reflection histogram data analysis", the "specular reflection residual histogram data analysis", the "diffused reflection histogram data analysis", and the "diffused reflection RGB data analysis" described above.

If the type of the recording medium M can be identified through the processing at Step S105 (Yes at Step S106), the colorimetric camera 20 transmits medium information indicating the identified type of the recording medium M to the FPGA for control 110 on the main control board 120 (Step S107). On the other hand, if the type of the recording medium M cannot be identified through the processing at Step S105 (No at Step S106), the colorimetric camera 20 transmits medium information indicating that the type of the recording medium M cannot be identified to the FPGA for control 110 on the main control board 120 (Step S108).

The following describes details about the processing at Step S105 with specific examples.

Specular Reflection Histogram Data Analysis

First, the following describes the "specular reflection histogram data analysis". As described above, the "specular reflection histogram data analysis" is processing of threshold determination of the peak value of the luminance histogram of the specular reflection region.

Figure 8A:
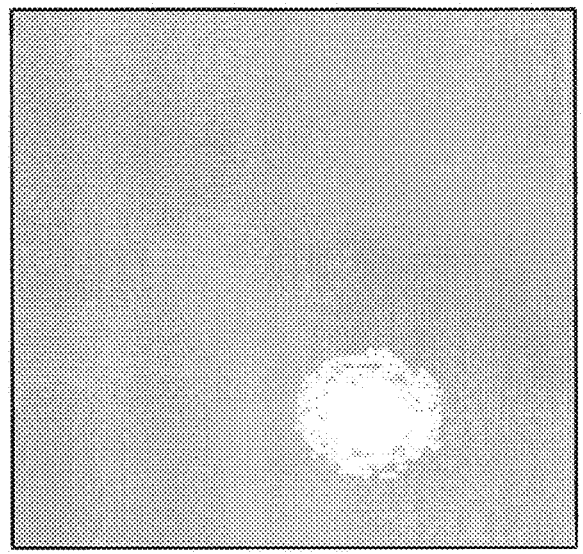
FIGS. 8A and 8B are diagrams illustrating an example of an image of a recording medium captured by a two-dimensional image sensor under illumination of a second light source.
Figure 8B:
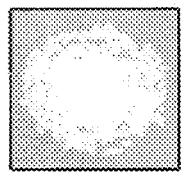

FIGS. 8A and 8B are diagrams illustrating an example of the image of the recording medium M captured by the two-dimensional image sensor 26 under the illumination of the second light source 32. FIG. 8A illustrates an example of the entire image of the recording medium M captured through the opening 25 of the housing 23. FIG. 8B illustrates an example of the image of the specular reflection region extracted from the example of the image in FIG. 8A. A position of the specular reflection region exemplified in FIG. 8B can be specified based on a positional relation between the second light source 32 and the two-dimensional image sensor 26. Accordingly, the identifying unit 47 can acquire the image data of the specular reflection region by extracting the image of the specular reflection region exemplified in FIG. 8B from the image exemplified in FIG. 8A.

In the "specular reflection histogram data analysis", the identifying unit 47 generates a luminance histogram from the image data of the specular reflection region illustrated in FIG. 8B. The luminance histogram represents a relation between a luminance value of the pixel included in the image and the frequency thereof (the number of pixels having the same luminance value). In the colorimetric camera 20 according to the embodiment, three types (R, G, and B) of luminance values can be acquired for each pixel because the two-dimensional image sensor 26 outputs RGB image data. However, only one of the luminance values may be used because the luminance values have similar tendency. In the embodiment, a luminance value of G (for example, 256 values represented by 8 bits) is used. The luminance value slightly varies depending on a surface shape of the platen 16 that supports the recording medium M when the two-dimensional image sensor 26 captures an image, but the variation is negligible. In the embodiment, it is assumed that the two-dimensional image sensor 26 captures an image of a portion of the recording medium M supported by the platen 16, the portion being positioned on a flat part (also referred to as a lateral rib part) other than a recessed part or a hole of the platen 16.

Figure 9:
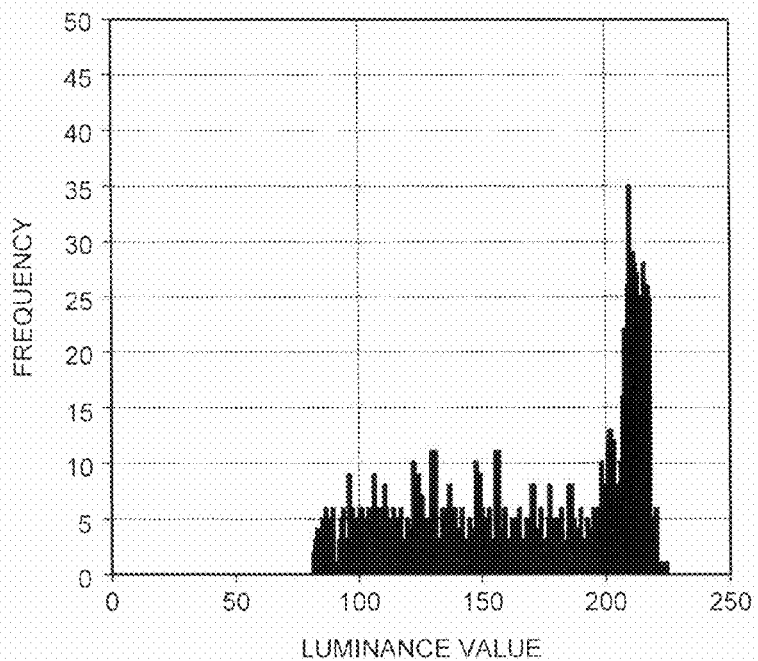
FIG. 9 is a diagram illustrating an example of a luminance histogram of a specular reflection region.

FIG. 9 is a diagram illustrating an example of the luminance histogram of the specular reflection region in which a horizontal axis represents the luminance value of the pixel (in the embodiment, 256 values of G), and a vertical axis represents the frequency. The identifying unit 47 generates the luminance histogram exemplified in FIG. 9 from the image data of the specular reflection region, and detects the peak value of the luminance histogram to perform threshold comparison. In this case, the peak value of the luminance histogram means the luminance value the frequency of which is the largest. The luminance histogram illustrated in FIG. 9 is an example of a case in which the type of the recording medium M is "glossy paper", and the peak value of the luminance histogram (the luminance value the frequency of which is the largest) is "210".

Figure 10:
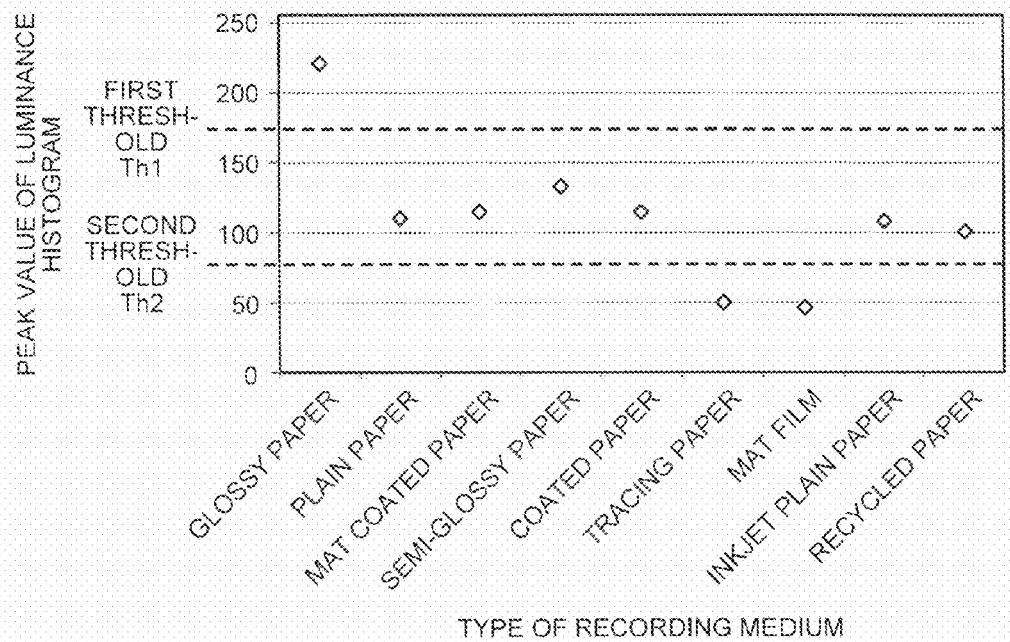
FIG. 10 is a diagram illustrating a relation between types of the recording media and a peak value of the luminance histogram of the specular reflection region.

FIG. 10 is a diagram illustrating a relation between the types of the recording media M and the peak value of the luminance histogram of the specular reflection region. When the peak value of the luminance histogram of the specular reflection region is detected for each of the nine types of recording media M described above, as illustrated in FIG. 10, a large value exceeding "200" is detected for the "glossy paper", and a small value such as about "50" is detected for each of the "tracing paper" and the "mat film". For each of the "plain paper", the "mat coated paper", the "semi-glossy paper", the "coated paper", the "inkjet plain paper", and the "recycled paper" other than the above, the peak values of the luminance histogram are detected in a range from "100" to "150". Accordingly, as illustrated in FIG. 10, for example, the identifying unit 47 sets a first threshold Th1 between "150" and "200" and sets a second threshold Th2 between "50" and "100", and compares the peak value of the luminance histogram obtained from the image data of the specular reflection region with the first threshold Th1 and the second threshold Th2 to identify whether the recording medium M is the "glossy paper", the "tracing paper", or the "mat film", or the other types.

That is, when the peak value of the luminance histogram obtained from the image data of the specular reflection region is larger than the first threshold Th1, the recording medium M can be determined to be the "glossy paper". When the peak value of the luminance histogram obtained from the image data of the specular reflection region is smaller than the second threshold Th2, the recording medium M can be determined to be the "tracing paper" or the "mat film". When the peak value of the luminance histogram obtained from the image data of the specular reflection region is between the first threshold Th1 and the second threshold Th2, the recording medium M can be determined to be any of the "plain paper", the "mat coated paper", the "semi-glossy paper", the "coated paper", the "inkjet plain paper", and the "recycled paper". Appropriate values for the first threshold Th1 and the second threshold Th2 are determined in advance and stored in the nonvolatile memory 45. In performing "specular reflection histogram data analysis", the identifying unit 47 reads out the first threshold Th1 and the second threshold Th2 from the nonvolatile memory 45 and set the first threshold Th1 and the second threshold Th2 as comparison targets of the peak value of the luminance histogram obtained from the image data of the specular reflection region. Information indicating a relation between the first threshold Th1 and the second threshold Th2, and the peak value of the luminance histogram of the specular reflection region (whether the peak value is larger or smaller than the threshold) is stored, for example, in the nonvolatile memory 45 in a format that can be referred to for each of the registered recording media M.

Diffused Reflection Histogram Data Analysis

Next, the following describes the "diffused reflection histogram data analysis". As described above, the "diffused reflection histogram data analysis" is processing of threshold comparison of the value of the standard deviation σ of the luminance histogram of the diffused reflection region.

Figure 11:
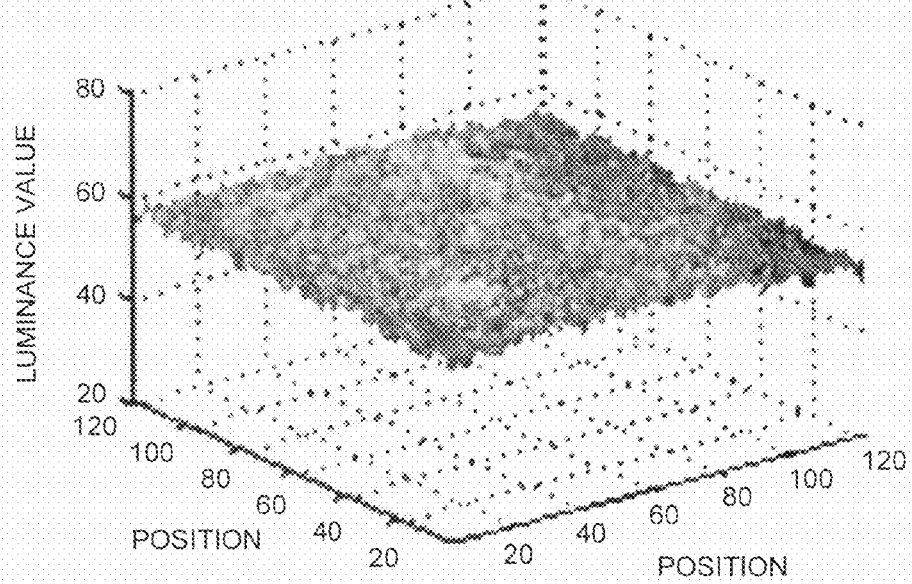
FIG. 11 is a diagram three-dimensionally illustrating a luminance distribution in a diffused reflection region in a case in which the recording medium is a "mat film"
Figure 12:
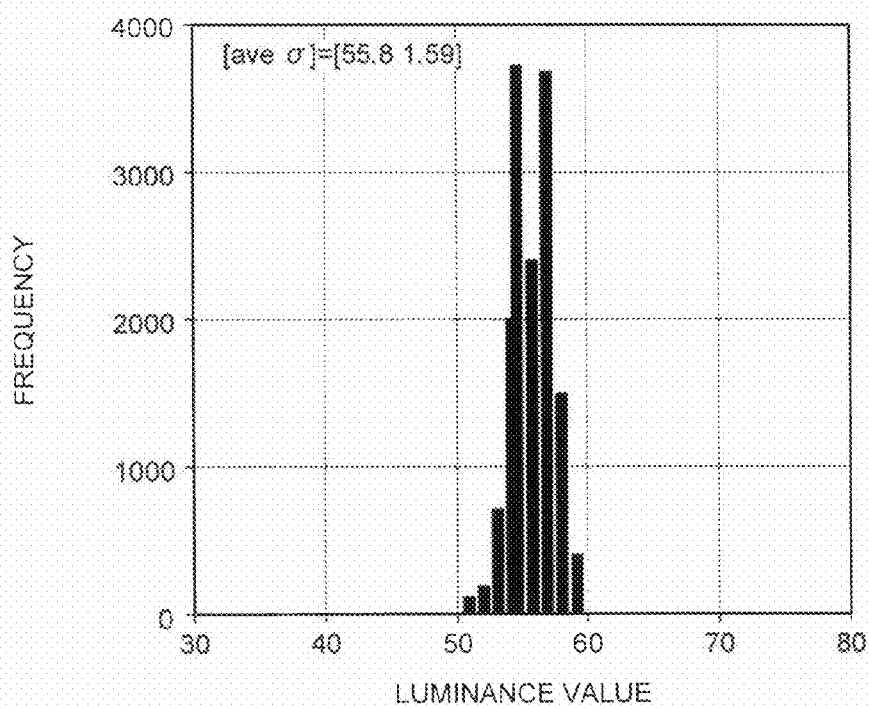
FIG. 12 is a diagram illustrating an example of the luminance histogram of the diffused reflection region.

In the "diffused reflection histogram data analysis", the identifying unit 47 generates the luminance histogram from the image data of the diffused reflection region. FIG. 11 is a diagram three-dimensionally illustrating the luminance distribution in the diffused reflection region in a case in which the recording medium M is the "mat film" in which each of two axes in the horizontal direction represents the position of the pixel in the diffused reflection region, and an axis in the vertical direction represents the luminance value of each pixel (in the embodiment, 256 values of G). FIG. 12 is a diagram illustrating an example of the luminance histogram of the diffused reflection region in a case in which the recording medium M is the "mat film". The identifying unit 47 generates the luminance histogram as illustrated in FIG. 12 from the image data of the diffused reflection region, and obtains the value of the standard deviation σ thereof. In the luminance histogram illustrated in FIG. 12, a value of an average ave is "55.8" and the value of the standard deviation σ is "1.59".

Figure 13:
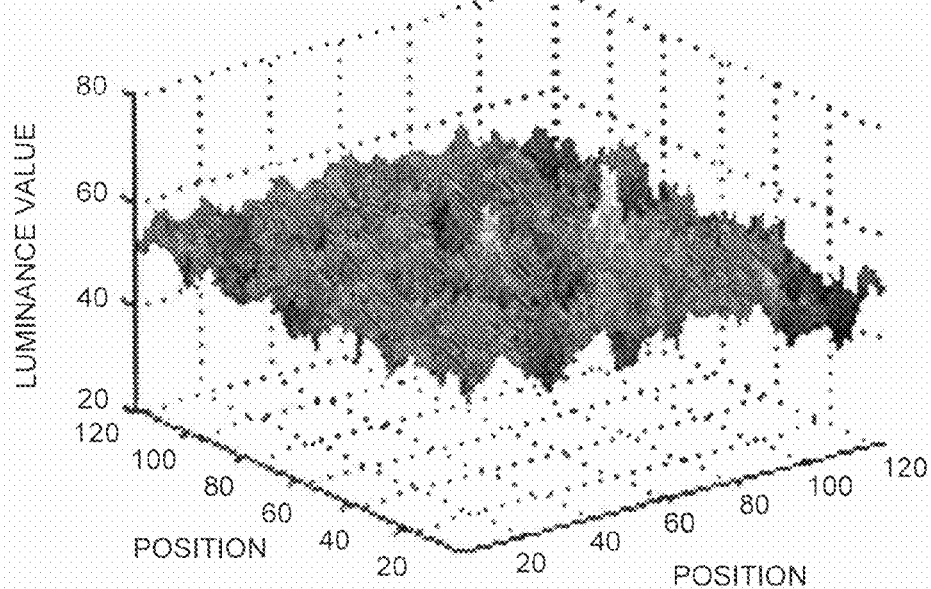
FIG. 13 is a diagram three-dimensionally illustrating the luminance distribution in the diffused reflection region in a case in which the recording medium is "tracing paper"
Figure 14:
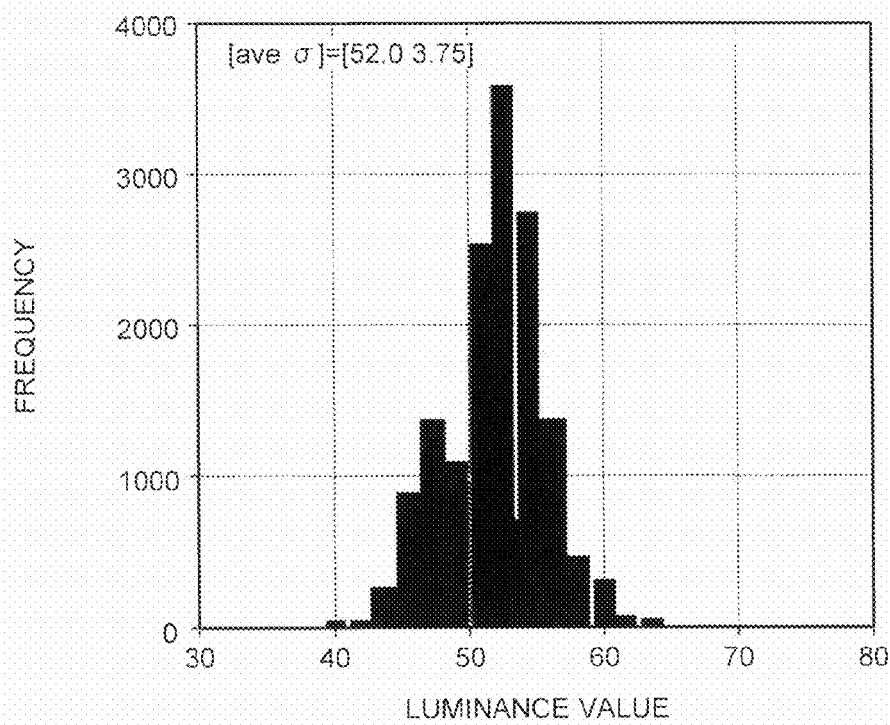
FIG. 14 is a diagram illustrating an example of the luminance histogram of the diffused reflection region.

FIG. 13 is a diagram three-dimensionally illustrating the luminance distribution in the diffused reflection region in a case in which the recording medium M is the "tracing paper" in which each of two axes in the horizontal direction represents the position of the pixel in the diffused reflection region, and an axis in the vertical direction represents the luminance value of each pixel (in the embodiment, 256 values of G). FIG. 14 is a diagram illustrating an example of the luminance histogram of the diffused reflection region in a case in which the recording medium M is the "tracing paper". The identifying unit 47 generates the luminance histogram as illustrated in FIG. 14 from the image data of the diffused reflection region, and obtains the value of the standard deviation σ thereof. In the luminance histogram illustrated in FIG. 14, the value of the average ave is "52.0" and the value of the standard deviation σ is "3.75".

Figure 15:
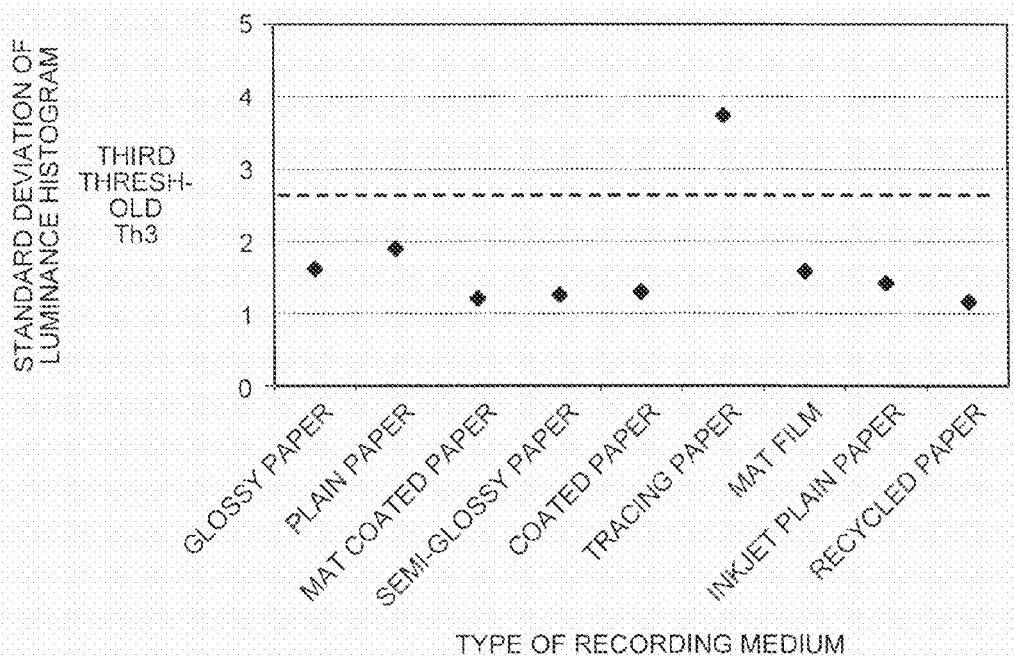
FIG. 15 is a diagram illustrating a relation between the types of the recording media and a value of a standard deviation of the luminance histogram of the diffused reflection region.

FIG. 15 is a diagram illustrating a relation between the types of the recording media M and the value of the standard deviation σ of the luminance histogram of the diffused reflection region. When the value of the standard deviation σ of the luminance histogram of the diffused reflection region is obtained for each of the nine types of recording media M described above, as illustrated in FIG. 15, a large value close to "4" is calculated for the "tracing paper", and a relatively small value in a range from "1" to "2" is calculated for each of the "glossy paper", the "plain paper", the "mat coated paper", the "semi-glossy paper", the "coated paper", the "mat film", the "inkjet plain paper", and the "recycled paper" other than the above. Accordingly, as illustrated in FIG. 15 for example, the identifying unit 47 sets a third threshold Th3 between "2" and "3", and compares the value of the standard deviation σ of the luminance histogram obtained from the image data of the diffused reflection region with the third threshold Th3 to identify whether the recording medium M is the "tracing paper" or the other types.

That is, when the value of the standard deviation σ of the luminance histogram obtained from the image data of the diffused reflection region is larger than the third threshold Th3, the recording medium M can be determined to be the "tracing paper". In a case in which the "diffused reflection histogram data analysis" is performed after the recording medium M is determined to be the "tracing paper" or the "mat film" through the "specular reflection histogram data analysis" described above, when the value of the standard deviation σ of the luminance histogram obtained from the image data of the diffused reflection region is smaller than the third threshold Th3, the recording medium M can be determined to be the "mat film". An appropriate value for the third threshold Th3 is determined in advance and stored in the nonvolatile memory 45. In performing "diffused reflection histogram data analysis", the identifying unit 47 reads out the third threshold Th3 from the nonvolatile memory 45 and sets he third threshold Th3 as a comparison target of the value of the standard deviation σ of the luminance histogram obtained from the image data of the diffused reflection region. Information indicating a relation between the third threshold Th3 and the value of the standard deviation σ of the luminance histogram of the diffused reflection region (whether the value is larger or smaller than the threshold) is stored, for example, in the nonvolatile memory 45 in a format that can be referred to for each of the registered recording media M.

Specular Reflection Residual Histogram Data Analysis

Next, the following describes the "specular reflection residual histogram data analysis". As described above, the "specular reflection residual histogram data analysis" is processing of threshold comparison of the value of the standard deviation σ of the histogram of the residual that is a difference between the luminance distribution in the specular reflection region and the normal distribution.

Figure 16:
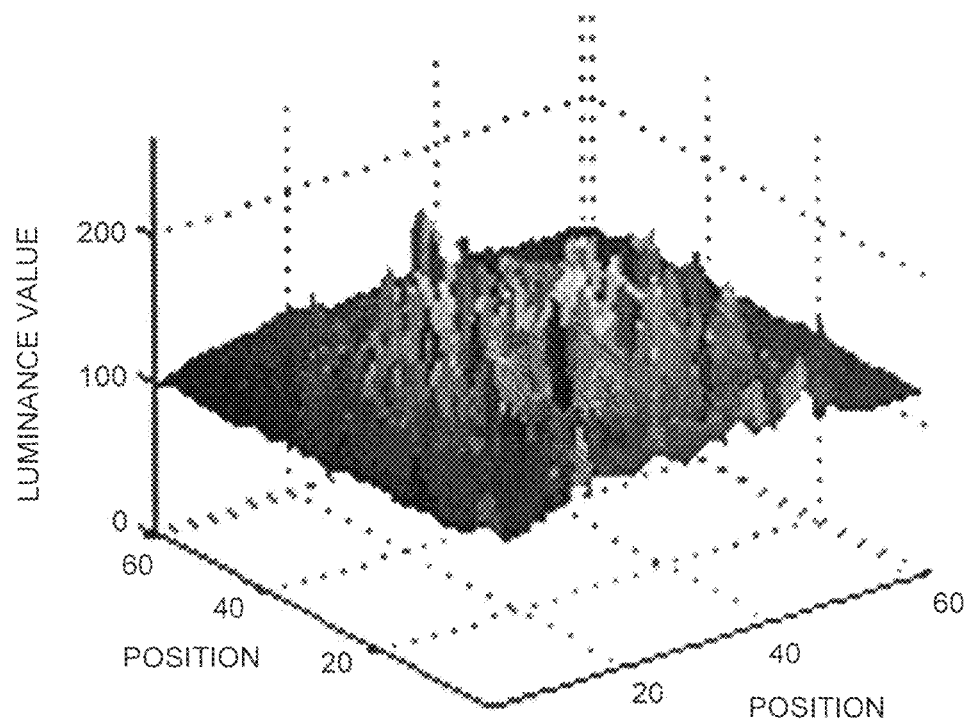
FIG. 16 is a diagram three-dimensionally illustrating the luminance distribution in the specular reflection region in a case in which the recording medium is "semi-glossy paper"
Figure 17:
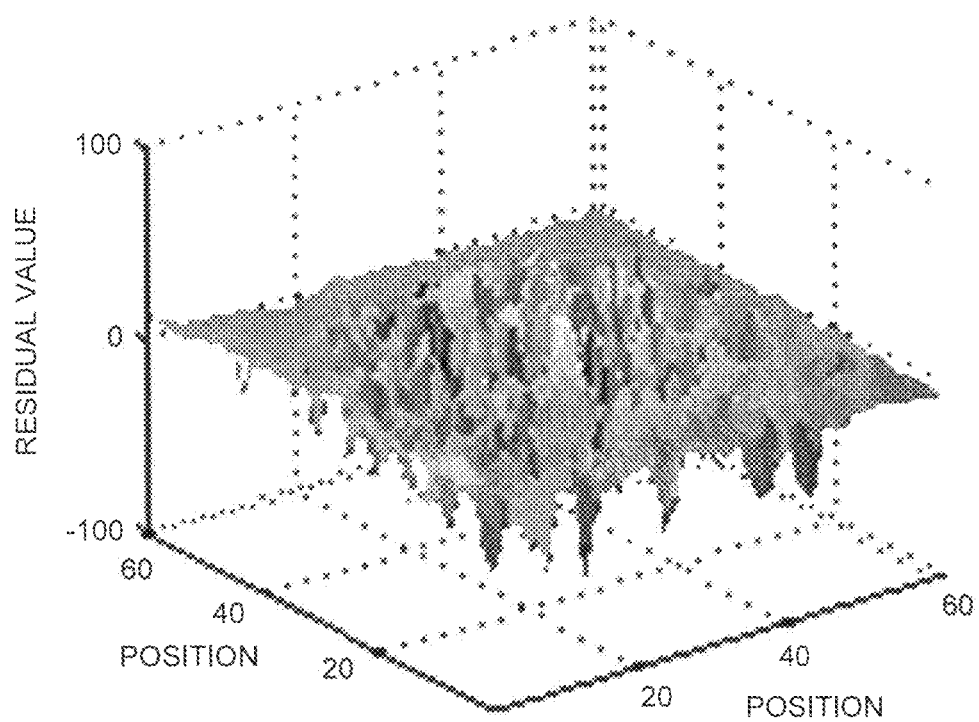
FIG. 17 is a diagram three-dimensionally illustrating a residual distribution.
Figure 18:
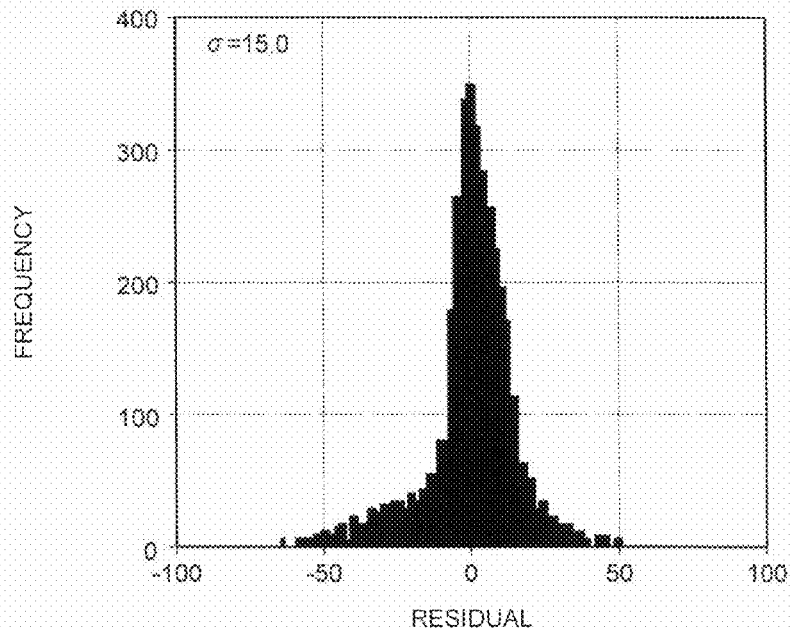
FIG. 18 is a diagram illustrating an example of a histogram of a residual.

In the "specular reflection residual histogram data analysis", the identifying unit 47 generates the histogram of the residual that is a difference between the luminance distribution in the specular reflection region and the normal distribution from the image data of the specular reflection region. FIG. 16 is a diagram three-dimensionally illustrating the luminance distribution in the specular reflection region in a case in which the recording medium M is the "semi-glossy paper". FIG. 17 is a diagram three-dimensionally illustrating a residual distribution. In FIGS. 16 and 17, each of two axes in the horizontal direction represents the position of the pixel in the specular reflection region. In FIG. 16, an axis in the vertical direction represents the luminance value of each pixel (in the embodiment, 256 values of G). In FIG. 17, an axis in the vertical direction represents a residual value of each pixel. FIG. 18 is a diagram illustrating an example of the histogram of the residual in a case in which the recording medium M is the "semi-glossy paper". The histogram of the residual represents a relation between the residual value of each pixel and the frequency thereof (the number of pixels having the same residual value) in the specular reflection region. The identifying unit 47 generates the histogram of the residual as illustrated in FIG. 18 from the image data of the specular reflection region, and obtains the value of the standard deviation σ thereof. In the histogram of the residual illustrated in FIG. 18, the value of the standard deviation σ is "15.0".

Figure 19:
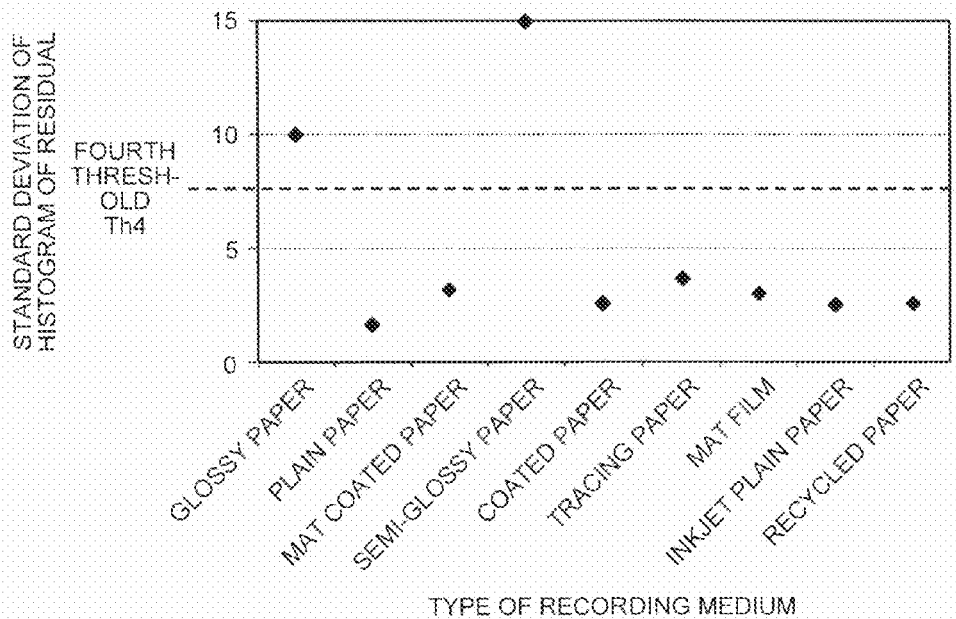
FIG. 19 is a diagram illustrating a relation between the types of the recording media and a value of a standard deviation of the histogram of the residuals of the specular reflection region.

FIG. 19 is a diagram illustrating a relation between the types of the recording media M and the value of the standard deviation σ of the histogram of the residual of the specular reflection region. When the value of the standard deviation σ of the histogram of the residual of the specular reflection region is obtained for each of the nine types of recording media M described above, as illustrated in FIG. 19, relatively large values such as "10" for the "glossy paper" and "15" for the "semi-glossy paper" are calculated, and a relatively small value equal to or smaller than "5" is calculated for the "plain paper", the "mat coated paper", the "coated paper", the "tracing paper", the "mat film", the "inkjet plain paper", and the "recycled paper" other than the above. Accordingly, as illustrated in FIG. 19, for example, the identifying unit 47 sets a fourth threshold Th4 between "5" and "10", and compares the value of the standard deviation σ of the histogram of the residual obtained from the image data of the specular reflection region with the fourth threshold Th4 to identify whether the recording medium M is the "glossy paper" or the "semi-glossy paper", or other types.

That is, when the value of the standard deviation σ of the histogram of the residual obtained from the image data of the specular reflection region is larger than the fourth threshold Th4, the recording medium M can be determined to be the "glossy paper" or the "semi-glossy paper". In a case in which the "specular reflection residual histogram data analysis" is performed after the recording medium M is determined to be any of the "plain paper", the "mat coated paper", the "semi-glossy paper", the "coated paper", the "inkjet plain paper", and the "recycled paper" through the "specular reflection histogram data analysis" described above, when the value of the standard deviation σ of the histogram of the residual obtained from the image data of the specular reflection region is larger than the fourth threshold Th4, the recording medium M can be determined to be the "semi-glossy paper". An appropriate value for the fourth threshold Th4 is determined in advance and stored in the nonvolatile memory 45. In performing "specular reflection residual histogram data analysis", the identifying unit 47 reads out the fourth threshold Th4 from the nonvolatile memory 45 and sets the fourth threshold Th4 as a comparison target of the value of the standard deviation σ of the histogram of the residual obtained from the image data of the specular reflection region. Information indicating a relation between the fourth threshold Th4 and the value of the standard deviation σ of the histogram of the residual (whether the value is larger or smaller than the threshold) is stored, for example, in the nonvolatile memory 45 in a format that can be referred to for each of the registered recording media M.

Diffused Reflection RGB Data Analysis

Next, the following describes the "diffused reflection RGB data analysis". As described above, the "diffused reflection RGB data analysis" is processing of collating the coordinate value of when the RGB value of the pixel included in the diffused reflection region is plotted in the RGB color space, with the coordinate range in the RGB color space set for each type of the registered recording medium M.

In the "diffused reflection RGB data analysis", the identifying unit 47 extracts the RGB value of an arbitrary pixel from the image data of the diffused reflection region. The RGB value extracted herein may be an RGB value of a specified pixel included in the diffused reflection region, an average value of RGB values of a plurality of specified pixels, or an average value of RGB values of all the pixels included in the diffused reflection region. The identifying unit 47 then identifies the type of the recording medium M by determining the type of the recording medium M to which a coordinate range among coordinate ranges set in the RGB color space corresponds, the coordinate range including the coordinate value of when the extracted RGB value is plotted in the RGB color space.

Figure 20A:
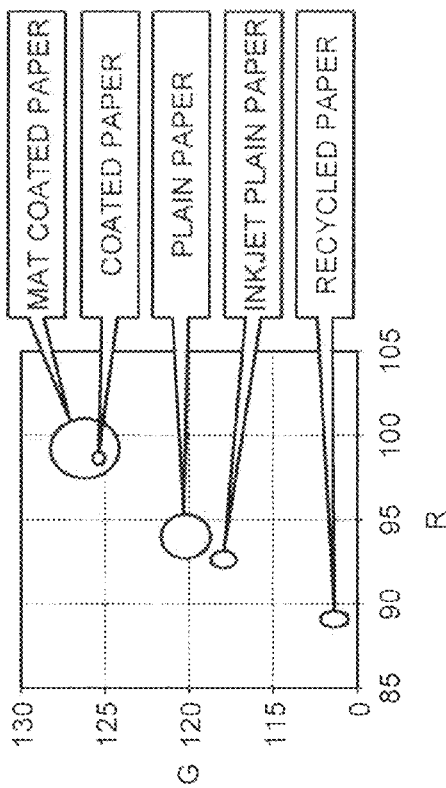
FIGS. 20A to 20D are diagrams illustrating a coordinate range in an RGB color space that is set for each type of the registered recording medium.
Figure 20B:
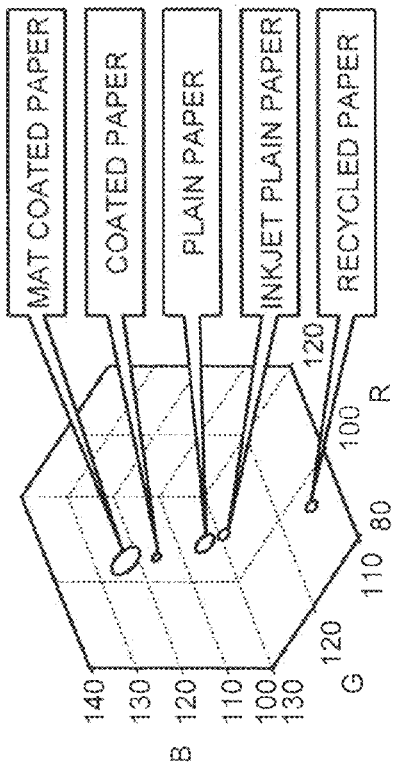
Figure 20C:
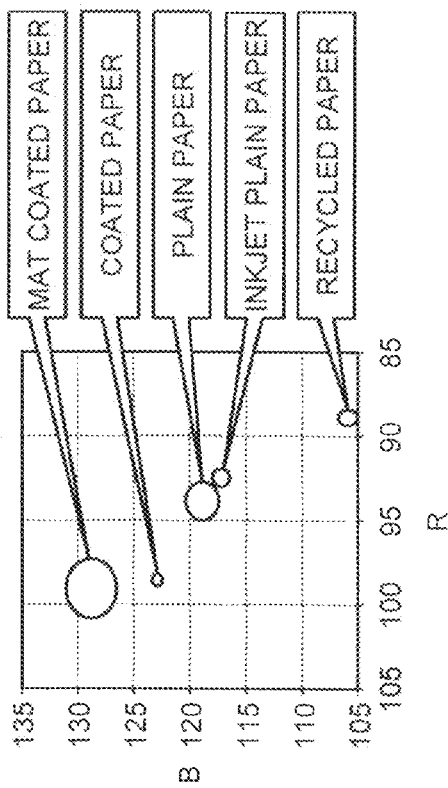
Figure 20D:
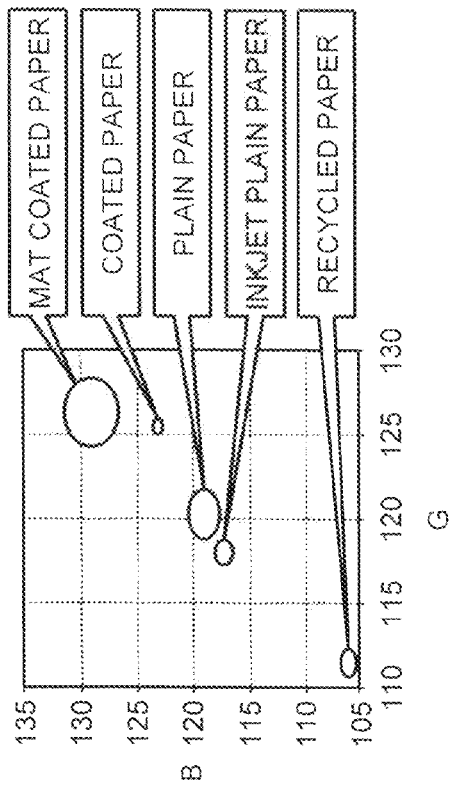

FIGS. 20A to 20D are diagrams illustrating the coordinate range in the RGB color space that is set for each type of the registered recording medium M. FIG. 20A illustrates the coordinate range in the RGB color space of the "plain paper", the "mat coated paper", the "coated paper", the "inkjet plain paper", and the "recycled paper" among the types of the registered recording media M, FIG. 20B illustrates a projection on an R-G plane, FIG. 20C illustrates a projection on a G-B plane, and FIG. 20D illustrates a projection on an R-B plane.

Each coordinate range illustrated in FIG. 20 is, for example, set as follows. That is, an image of each recording medium M is captured by the two-dimensional image sensor 26 a certain number of times (for example, thirty times) under the illumination of the first light source 31 in advance. The RGB value is extracted from each of the certain number of pieces of the obtained image data of the diffused reflection region, and a range of $2\sigma$ of a distribution thereof is obtained and stored in the nonvolatile memory 45. In performing "diffused reflection RGB data analysis", the identifying unit 47 reads out, from the nonvolatile memory 45, the range of $2\sigma$ obtained in advance for each type of the recording medium M to be set in the RGB color space. The identifying unit 47 then identifies the type of the recording medium M by determining the coordinate range set in the RGB color space in which the RGB value extracted from the image data of the diffused reflection region is included.

Among the nine types of recording media M described in this embodiment, five types including the "plain paper", the "mat coated paper", the "coated paper", the "inkjet plain paper", and the "recycled paper" cannot be uniquely identified through the "specular reflection histogram data analysis", the "diffused reflection histogram data analysis", and the "specular reflection residual histogram data analysis" described above. However, respective coordinate ranges in the RGB color space corresponding to the "plain paper", the "mat coated paper", the "coated paper", the "inkjet plain paper", and the "recycled paper" do not interfere with each other, and are separated from each other in the RGB color space, so that these types can be identified through the "diffused reflection RGB data analysis".

The colorimetric camera 20 according to the embodiment includes the colorimetric operation unit 44 that converts the RGB value into the colorimetric value such as the L*a*b* value. Accordingly, the identifying unit 47 can perform processing similar to the "diffused reflection RGB data analysis" using the L*a*b* value in place of the RGB value. Hereinafter, this processing is called "diffused reflection L*a*b* data analysis".

Diffused Reflection L*a*b* Data Analysis

The "diffused reflection L*a*b* data analysis" is processing of collating a coordinate value of when the L*a*b* value of the pixel included in the diffused reflection region is plotted in the L*a*b* color space with a coordinate range in the L*a*b* color space that is set for each type of the registered recording medium M.

In the "diffused reflection L*a*b* data analysis", the identifying unit 47 extracts the RGB value of an arbitrary pixel from the image data of the diffused reflection region. The value extracted herein may be an RGB value of a specified pixel included in the diffused reflection region, an average value of RGB values of a plurality of specified pixels, or an average value of RGB values of all the pixels included in the diffused reflection region. The identifying unit 47 then passes the extracted RGB value to the colorimetric operation unit 44, requests the colorimetric operation unit 44 to convert the RGB value into the L*a*b* value, and acquires, from the colorimetric operation unit 44, the L*a*b* value converted from the RGB value. The identifying unit 47 then identifies the type of the recording medium M by determining the type of the recording medium M to which a coordinate range among coordinate ranges set in the L*a*b* color space corresponds, the coordinate range including the coordinate value of when the acquired L*a*b* value is plotted in the L*a*b* color space.

FIGS. 21A to 21D are diagrams illustrating a coordinate range in the L*a*b* color space that is set for each type of the registered recording medium M. FIG. 21A illustrates the coordinate range in the L*a*b* color space of the "plain paper", the "mat coated paper", the "coated paper", the "inkjet plain paper", and the "recycled paper" among the types of the registered recording media M, FIG. 21B illustrates a projection on an a*-b* plane, FIG. 21C illustrates a projection on a b*-L* plane, and FIG. 21D illustrates a projection on an a*-L* plane.

Each coordinate range illustrated in FIG. 21 is, for example, set as follows. That is, an image of each recording medium M is captured by the two-dimensional image sensor 26 a certain number of times (for example, thirty times) under the illumination of the first light source 31 in advance. The RGB value is extracted from each of the certain number of pieces of the obtained image data of the diffused reflection region and converted into the L*a*b* value. Then, a range of $2\sigma$ of a distribution thereof is obtained and stored in the nonvolatile memory 45. In performing "diffused reflection L*a*b* data analysis", the identifying unit 47 reads out, from the nonvolatile memory 45, the range of $2\sigma$ obtained in advance for each type of the recording medium M to be set in the L*a*b* color space. The identifying unit 47 then identifies the type of the recording medium M by determining the coordinate range set in the L*a*b* color space in which the L*a*b* value converted from the RGB value that is extracted from the image data of the diffused reflection region is included.

Among the nine types of recording media M described in this embodiment, five types including the "plain paper", the "mat coated paper", the "coated paper", the "inkjet plain paper", and the "recycled paper" cannot be uniquely identified through the "specular reflection histogram data analysis", the "diffused reflection histogram data analysis", and the "specular reflection residual histogram data analysis" described above. However, respective coordinate ranges in the L*a*b* color space corresponding to the "plain paper", the "mat coated paper", the "coated paper", the "inkjet plain paper", and the "recycled paper" do not interfere with each other, and are separated from each other in the L*a*b* color space, so that these types can be identified through the "diffused reflection L*a*b* data analysis".

Specific Example of Processing Procedure of Identifying Unit

Figure 22:
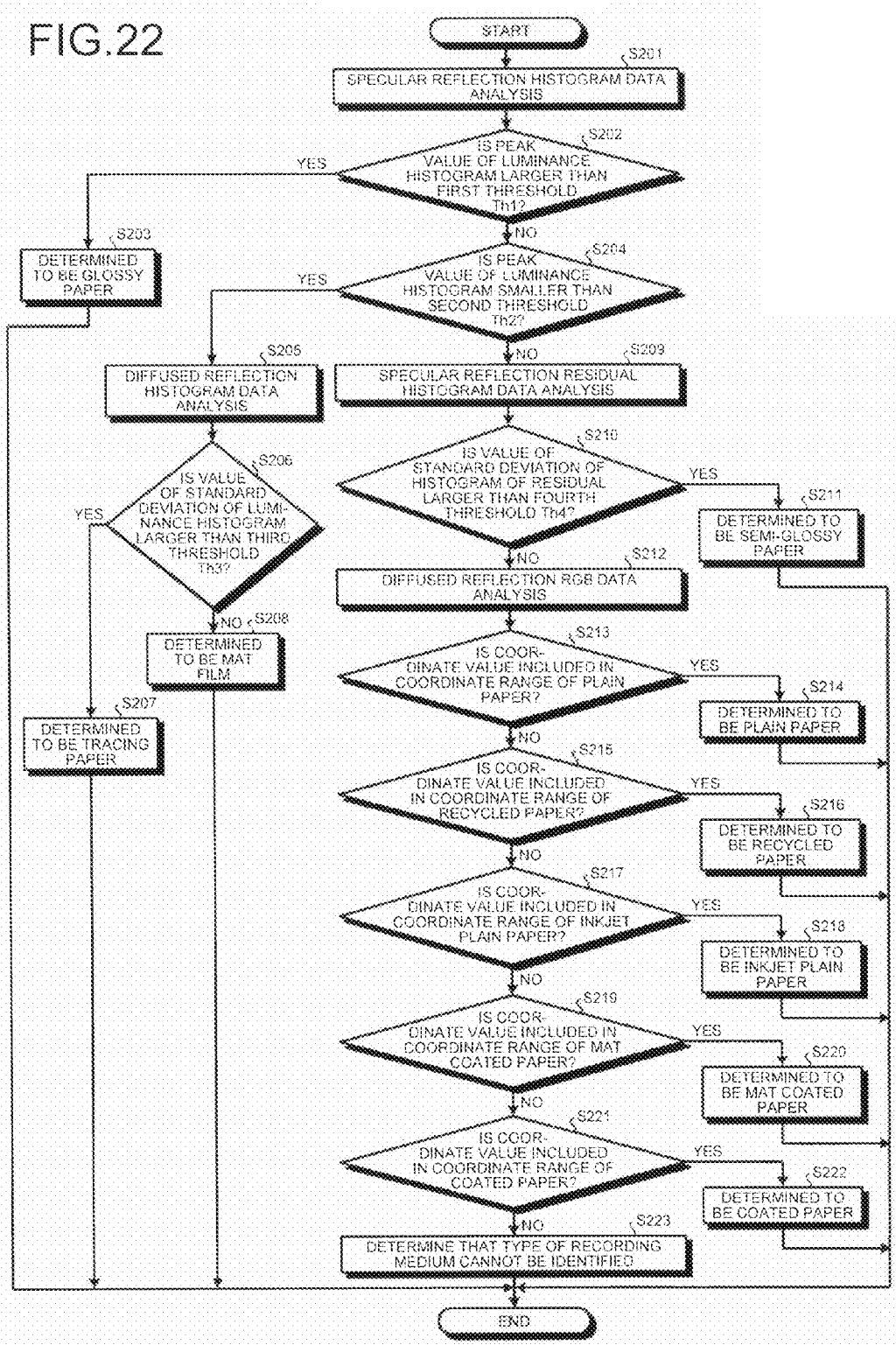
FIG. 22 is a flowchart illustrating an example of a processing procedure performed by an identifying unit.

Next, the following describes a specific example of a processing procedure (the processing procedure at Step S105 in FIG. 7) performed by the identifying unit 47 with reference to FIG. 22. FIG. 22 is a flowchart illustrating an example of the processing procedure performed by the identifying unit 47.

The identifying unit 47 first performs "specular reflection histogram data analysis" (Step S201), and determines whether the peak value of the luminance histogram obtained from the image data of the specular reflection region is larger than the first threshold Th1 (Step S202). If the peak value is larger than the first threshold Th1 (Yes at Step S202), the identifying unit 47 determines that the recording medium M is the "glossy paper" (Step S203), and ends the processing.

On the other hand, if the peak value of the luminance histogram obtained from the image data of the specular reflection region is equal to or smaller than the first threshold Th1 (No at Step S202), the identifying unit 47 determines whether the peak value is smaller than the second threshold Th2 (Step S204). If the peak value is smaller than the second threshold Th2 (Yes at Step S204), the identifying unit 47 then performs "diffused reflection histogram data analysis" (Step S205), and determines whether the value of the standard deviation σ of the luminance histogram obtained from the image data of the diffused reflection region is larger than the third threshold Th3 (Step S206). If the value of the standard deviation σ is larger than the third threshold Th3 (Yes at Step S206), the identifying unit 47 determines that the recording medium M is the "tracing paper" (Step S207), and ends the processing. On the other hand, if the value of the standard deviation σ is equal to or smaller than the third threshold Th3 (No at Step S206), the identifying unit 47 determines that the recording medium M is the "mat film" (Step S208), and ends the processing.

On the other hand, at the determination at Step S204, if the peak value of the luminance histogram obtained from the image data of the specular reflection region is equal to or larger than the second threshold Th2 (No at Step S204), the identifying unit 47 then performs "specular reflection residual histogram data analysis" (Step S209), and determines whether the value of the standard deviation σ of the histogram of the residual obtained from the image data of the specular reflection region is larger than the fourth threshold Th4 (Step S210). If the value of the standard deviation σ of the histogram of the residual is larger than the fourth threshold Th4 (Yes at Step S210), the identifying unit 47 determines that the recording medium M is the "semi-glossy paper" (Step S211), and ends the processing.

On the other hand, if the value of the standard deviation σ of the histogram of the residual is equal to or smaller than the fourth threshold Th4 (No at Step S210), the identifying unit 47 then performs "diffused reflection RGB data analysis" (Step S212), and determines the type of the recording medium M to which a coordinate range among coordinate ranges set in the RGB color space corresponds, the coordinate range including the coordinate value of when the RGB value extracted from the image data of the diffused reflection region is plotted in the RGB color space. If the coordinate value is included in the coordinate range corresponding to the "plain paper" (Yes at Step S213), the identifying unit 47 determines that the recording medium M is the "plain paper" (Step S214), and ends the processing. If the coordinate value is included in the coordinate range corresponding to the "recycled paper" (Yes at Step S215), the identifying unit 47 determines that the recording medium M is the "recycled paper" (Step S216), and ends the processing. If the coordinate value is included in the coordinate range corresponding to the "inkjet plain paper" (Yes at Step S217), the identifying unit 47 determines that the recording medium M is the "inkjet plain paper" (Step S218), and ends the processing. If the coordinate value is included in the coordinate range corresponding to the "mat coated paper" (Yes at Step S219), the identifying unit 47 determines that the recording medium M is the "mat coated paper" (Step S220), and ends the processing. If the coordinate value is included in the coordinate range corresponding to the "coated paper" (Yes at Step S221), the identifying unit 47 determines that the recording medium M is the "coated paper" (Step S222), and ends the processing. If the coordinate value is not included in any of the coordinate ranges (No at Step S213, No at Step S215, No at Step S217, No at Step S219, and No at Step S221), the identifying unit 47 determines that the type of the recording medium M cannot be identified (Step S223), and ends the processing.

FIG. 23 is a diagram for explaining a relation between an example of the processing procedure performed by the identifying unit 47 and identification results in a case in which the processing is performed in the order of the "specular reflection histogram data analysis", the "diffused reflection histogram data analysis", the "specular reflection residual histogram data analysis", and the "diffused reflection RGB data analysis".

Through the "specular reflection histogram data analysis", the types of the recording media M can be classified into three, that is, A1, B1, and C1 illustrated in FIG. 23. The recording medium M classified as A1 is only the "glossy paper". Accordingly, when the recording medium M is the "glossy paper", the identification process is ended at this phase.

Next, through the "diffused reflection histogram data analysis", the types of the recording media M can be classified into two, that is, A2 and B2 illustrated in FIG. 23. The recording medium M classified as A2 is only the "tracing paper". Accordingly, when the recording medium M is the "tracing paper", the identification process is ended at this phase. Among the recording media M classified as B2, the recording medium M classified as B1 through the above "specular reflection histogram data analysis" is only the "mat film". Accordingly, when the recording medium M is the "mat film", the identification process is ended at this phase.

Next, through the "specular reflection residual histogram data analysis", the types of the recording media M can be classified into two, that is, A3 and B3 illustrated in FIG. 23. The recording medium M classified as A3 is only the "glossy paper" and the "semi-glossy paper", and the "glossy paper" is identified through the above "specular reflection histogram data analysis". Accordingly, when the recording medium M is the "semi-glossy paper", the identification process is ended at this phase.

Next, through the "diffused reflection RGB data analysis", the five types (A4, B4, C4, D4, and E4 illustrated in FIG. 23) that have not been identified can be identified. When the recording medium M is any of the "plain paper", the "recycled paper", the "inkjet plain paper", the "mat coated paper", and the "coated paper", the identification process is ended at this phase.

The order of the processing procedure performed by the identifying unit 47 is not limited to the example described above. For example, the "specular reflection residual histogram data analysis" may be performed first. FIG. 24 illustrates an example of a case in which the identifying unit 47 performs the processing in the order of the "specular reflection residual histogram data analysis", the "specular reflection histogram data analysis", the "diffused reflection histogram data analysis", and the "diffused reflection RGB data analysis".

In this case, first, the types of the recording media M may be classified into two types, that is, A1 and B1 illustrated in FIG. 24 through the "specular reflection residual histogram data analysis".

Next, the types of the recording media M can be classified into three types, that is, A2, B2, and C2 illustrated in FIG. 24 through the "specular reflection histogram data analysis". The recording medium M classified as A2 is only the "glossy paper". Accordingly, when the recording medium M is the "glossy paper", the identification process is ended at this phase. Among the recording media M classified as C2, the recording medium M classified as A1 through the above "specular reflection residual histogram data analysis" is only the "semi-glossy paper". Accordingly, when the recording medium M is the "semi-glossy paper", the identification process is ended at this phase.

Next, through the "diffused reflection histogram data analysis", the types of the recording media M can be classified into two types, that is, A3 and B3 illustrated in FIG. 24.

The recording medium M classified as A3 is only the "tracing paper". Accordingly, when the recording medium M is the "tracing paper", the identification process is ended at this phase. Among the recording media M classified as B3, the recording medium M classified as B2 through the above "specular reflection histogram data analysis" is only the "mat film". Accordingly, when the recording medium M is the "mat film", the identification process is ended at this phase.

Next, through the "diffused reflection RGB data analysis", the five types (A4, B4, C4, D4, and E4 illustrated in FIG. 24) that have not been identified can be identified. When the recording medium M is any of the "plain paper", the "recycled paper", the "inkjet plain paper", the "mat coated paper", and the "coated paper", the identification process is ended at this phase.

When the identifying unit 47 identifies the type of the recording medium M as described above, medium information indicating the type of the recording medium M is transmitted from the colorimetric camera 20 to the ink discharge control unit 113 in the FPGA for control 110. The ink discharge control unit 113 in the FPGA for control 110 selects a printing type appropriate for the type of the recording medium M indicated by the medium information. The printing type includes a discharging type of the ink discharged onto the recording medium M and resolution of the image formed on the recording medium M.

FIG. 25 is a diagram illustrating a relation between an optimum printing type, and the types of the recording media and printing modes. FIG. 26 is a diagram illustrating the discharging type and the resolution corresponding to each printing type. As illustrated in FIG. 26, a printing type A is a type in which the recording head 6 discharges large droplets of ink to form an image on the recording medium M with the resolution of 600 dpi. A printing type B is a type in which the recording head 6 discharges middle droplets of ink to form an image on the recording medium M with the resolution of 600 dpi. A printing type C is a type in which the recording head 6 discharges small droplets of ink to form an image on the recording medium M with the resolution of 600 dpi. A printing type D is a type in which the recording head 6 discharges middle droplets of ink to form an image on the recording medium M with the resolution of 1200 dpi. A printing type E is a type in which the recording head 6 discharges small droplets of ink to form an image on the recording medium M with the resolution of 1200 dpi.

As illustrated in FIG. 25, the ink discharge control unit 113 selects any of the printing types A to E described above based on the type of the recording medium M indicated by the medium information from the colorimetric camera 20 and a designated printing mode, and determines the discharging type of the ink to be discharged onto the recording medium M and the resolution of the image to be formed on the recording medium M. Four types of printing modes are prepared, that is, "fast (line drawing)", "fast", "standard", and "high quality" in descending order of printing speed, and any of the printing modes is designated by the user in advance. When the printing mode is not designated by the user, as illustrated in FIG. 27, for example, a printing mode predetermined for each type of the recording medium M is automatically set. FIG. 27 is a diagram illustrating a relation between the type of the recording medium M and the printing mode that is automatically set.

For example, in a case in which the identified type of the recording medium M is any of the "plain paper", the "recycled paper", and the "inkjet plain paper", the printing type A is selected when the printing mode is "fast (line drawing)", and the printing type B is selected when the printing mode is other than "fast (line drawing)". When the identified type of the recording medium M is the "tracing paper", the printing mode of "fast (line drawing)" is not applied thereto, so that the printing type B is selected irrespective of the printing mode.

In a case in which the identified type of the recording medium M is the "mat film", the printing type B is selected when the printing mode is "standard", and the printing type C is selected when the printing mode is "high quality". The printing modes of "fast (line drawing)" and "fast" are not applied to the "mat film".

In a case in which the identified type of the recording medium M is the "mat coated paper", the printing type A is selected when the printing mode is "fast (line drawing)", the printing type C is selected when the printing mode is "fast", the printing type B is selected when the printing mode is "standard", and the printing type D is selected when the printing mode is "high quality".

In a case in which the identified type of the recording medium M is the "coated paper", the printing type C is selected when the printing mode is "fast", the printing type B is selected when the printing mode is "standard", and the printing type D is selected when the printing mode is "high quality". The printing mode of "fast (line drawing)" is not applied to the "coated paper".

When the identified type of the recording medium M is the "glossy paper", the printing mode that supports the "glossy paper" is only "high quality", so that the printing type E is selected. In a case in which the identified type of the recording medium M is the "semi-glossy paper", the printing type C is selected when the printing mode is "fast", the printing type B is selected when the printing mode is "standard", and the printing type E is selected when the printing mode is "high quality". The printing mode of "fast (line drawing)" is not applied to the "semi-glossy paper".

According to the embodiment, the ink discharge control unit 113 in the FPGA for control 110 determines the discharging type and the resolution according to the type of the recording medium M identified by the identifying unit 47. Alternatively, the discharging type and the resolution may be determined by the CPU 101. In this case, the ink discharge control unit 113 controls the operation of the recording head 6 to perform image formation on the recording medium M with the discharging type and the resolution determined by the CPU 101 in accordance with a command from the CPU 101.

When the identifying unit 47 cannot identify the type of the recording medium M, as described above, the medium information indicating that the type of the recording medium M cannot be identified is transmitted from the colorimetric camera 20 to the notification unit 116 in the FPGA for control 110. In this case, for example, the notification unit 116 causes the operation panel 17 to display a predetermined message to notify the user using the image forming apparatus 100 that the type of the recording medium M cannot be identified, that is, the recording medium M used for image formation is a recording medium M unknown to the image forming apparatus 100. Through this notifying operation of the notification unit 116, the user can recognize that the recording medium M is unknown to the image forming apparatus 100. In this case, for example, when information for identifying the type of the unknown recording medium M is registered, identification by the identifying unit 47 is enabled from this point forward.

FIG. 28 is a flowchart illustrating an example of processing of generating and storing the information for identifying the type of the unknown recording medium M, and specifically illustrates a processing procedure for storing, in the nonvolatile memory 45, the range of 2σ indicating the coordinate range in the RGB color space used for the "diffused reflection RGB data analysis". The processing illustrated in the flowchart of FIG. 28 is performed such that the user performs a predetermined input operation through the operation panel 17 to operate the image forming apparatus 100 in a registration mode, for example.

First, the unknown recording medium M is set at a predetermined position on the platen 16 (Step S301). The image of the recording medium M is captured by the two-dimensional image sensor 26 of the colorimetric camera 20 mounted on the carriage 5 (Step S302), and the image data of the diffused reflection region is stored (Step S303). Next, it is determined whether a predetermined number (for example, thirty) of pieces of image data of the diffused reflection region are stored (Step S304). If the number of pieces of stored image data is smaller than the predetermined number (No at Step S304), an image capturing position on the recording medium M is changed by moving the carriage 5 (Step S305), and the processing after Step S302 is repeated. If the number of pieces of stored image data reaches the predetermined number (Yes at Step S304), the RGB value is extracted from each of the predetermined number of pieces of image data of the diffused reflection region, and the range of $2\sigma$ of distribution thereof is calculated (Step S306). The calculated range of $2\sigma$ is then stored in the nonvolatile memory 45 in association with the type of the recording medium M (Step S307).

The processing of storing, in the nonvolatile memory 45, the range of $2\sigma$ indicating the coordinate range in the RGB color space used for the "diffused reflection RGB data analysis" has been described above. To store, in the nonvolatile memory 45, the range of $2\sigma$ indicating the coordinate range in the L*a*b* color space used for the "diffused reflection L*a*b* data analysis", the range of $2\sigma$ may be calculated and stored in the nonvolatile memory 45 after converting the RGB value into the L*a*b* value. As information related to the "specular reflection histogram data analysis", the "diffused reflection histogram data analysis", and the "specular reflection residual histogram data analysis", a relation between the values of the recording medium M (the peak value of the luminance histogram of the specular reflection region, the value of the standard deviation $\sigma$ of the luminance histogram of the diffused reflection region, and the value of the standard deviation $\sigma$ of the histogram of the residual) obtained through the above processing, and the first threshold Th1, the second threshold Th2, the third threshold Th3, and the fourth threshold Th4 may be obtained and stored.

FIG. 29 is a flowchart illustrating an operation of the image forming apparatus 100 after the processing of identifying the type of the recording medium M is ended.

If the type of the recording medium M can be identified by the identifying unit 47 (Yes at Step S401), the ink discharge control unit 113 selects the printing type appropriate for the type of the recording medium M indicated by the medium information, and determines the discharging type of the ink to be discharged onto the recording medium M and the resolution of the image to be formed on the recording medium M (Step S402). According to the discharging type and the resolution determined at Step S402, printing on the recording medium M is started (Step S403).

On the other hand, if the type of the recording medium M cannot be identified (No at Step S401), for example, the notification unit 116 causes the operation panel 17 to display a predetermined message to notify the user that the type of the recording medium M cannot be identified (Step S404), and determines whether to continue the printing (Step S405). The determination for continuing the printing can be made, for example, according to whether the user performs a certain operation for instructing to continue the printing using the operation panel 17.

If the printing is continued (Yes at Step S405), various settings about the recording medium M are made to be settings for the "plain paper" (Step S406), the ink discharge control unit 113 selects the printing type appropriate for the "plain paper" at Step S402 and determines the discharging type and the resolution, and the printing on the recording medium M is started according to the discharging type and the resolution appropriate for the "plain paper" at Step S403. On the other hand, if the printing is not continued (No at Step S405), the processing is ended as it is.

As described in detail above with specific examples, according to the embodiment, the image of the recording medium M is captured by the two-dimensional image sensor 26, and the glossiness evaluation value indicating the glossiness of the recording medium M, the surface roughness evaluation value indicating the surface roughness of the recording medium M, and the coloring evaluation value indicating the coloring of the recording medium M are obtained using the image data of the specular reflection region and the image data of the diffused reflection region in the image of the recording medium M. The type of the recording medium M is then identified by combining the determination using the glossiness evaluation value, the determination using the surface roughness evaluation value, and the determination using the coloring evaluation value. Accordingly, the type of the recording medium M that could not be identified in the related art is enabled to be identified, so that more various types of recording media M can be appropriately identified than in the related art.

According to the embodiment, determination can be performed with higher accuracy to obtain an accurate evaluation value by acquiring the image data of the diffused reflection region from the image of the recording medium M captured under the illumination of the first light source 31 that is arranged so that the specular reflection light from the recording medium M is not incident on the two-dimensional image sensor 26, and acquiring the image data of the specular reflection region from the image of the recording medium M captured under the illumination of the second light source 32 that is arranged so that the specular reflection light from the recording medium M is incident on the two-dimensional image sensor 26.

According to the embodiment, optimum image formation can be performed on the recording medium M to be used by determining, for example, the discharging type of the ink to be discharged onto the recording medium M and the resolution of the image to be formed on the recording medium M according to the identified type of the recording medium M.

According to the embodiment, the user can recognize that the recording medium M to be used for image formation is the recording medium M unknown to the image forming apparatus 100 by receiving a notification indicating that the type of the recording medium M cannot be identified, and the user can determine whether to continue the printing, for example.

When the type of the recording medium M cannot be identified, information used for identifying the type of the unknown recording medium M is generated to be stored in a storage unit such as the nonvolatile memory 45 in accordance with the operation by the user. Accordingly, this type of recording medium M can be appropriately identified using the information from this point forward.

Modification of Colorimetric Camera

The following describes modifications (a first modification and a second modification) of the calorimetric camera 20 according to the embodiment. Hereinafter, the calorimetric camera 20 according to the first modification is referred to as a colorimetric camera 20A, and the calorimetric camera 20 according to the second modification is referred to as a colorimetric camera 20B. In each modification, a component common to that of the colorimetric camera 20 is denoted by the same reference sign, and redundant description will not be repeated.

First Modification

Figure 30A:
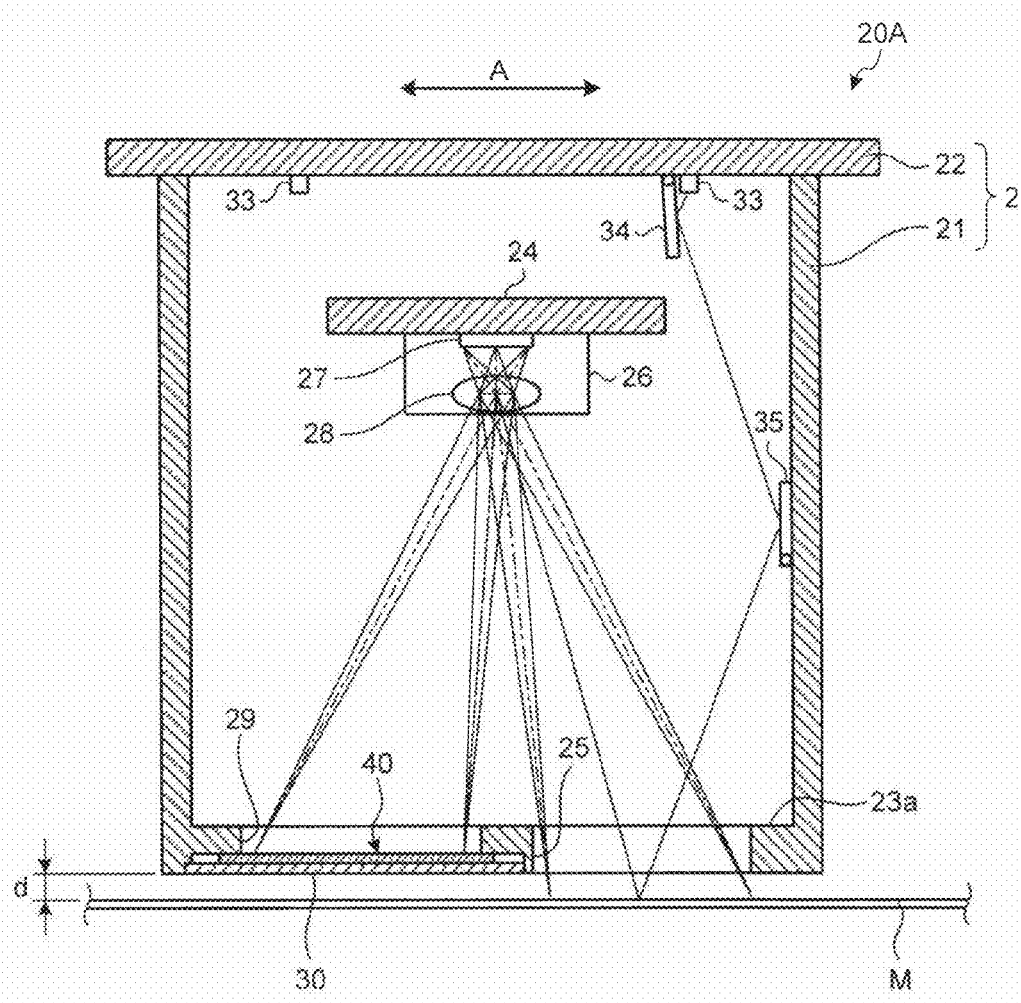
FIG. 30A is a vertical cross-sectional view of a colorimetric camera according to a first modification.
Figure 30B:
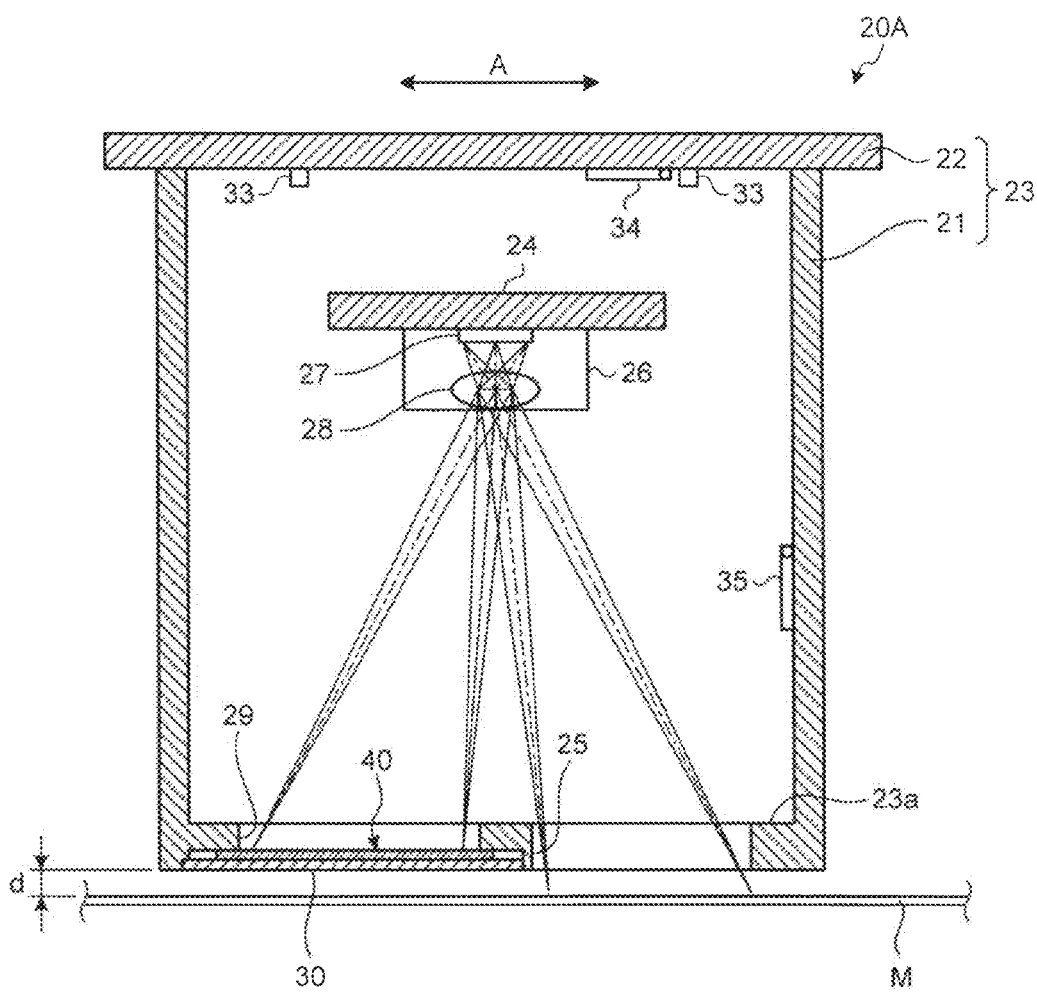
FIG. 30B is a vertical cross-sectional view of the colorimetric camera according to the first modification.

FIGS. 30A and 30B are vertical cross-sectional views of the colorimetric camera 20A according to the first modification. The colorimetric camera 20A according to the first modification includes common light sources 33 in place of the first light source 31 and the second light source 32 in the colorimetric camera 20 described above. Similarly to the first light source 31 described above, the common light sources 33 are positioned so that the specular reflection light from the recording medium M outside the housing 23 and the specular reflection light from the reference chart 40 inside the housing 23 are not incident on the two-dimensional image sensor 26.

The colorimetric camera 20A according to the first modification includes optical path changing mirrors 34 and 35 arranged therein for changing an optical path of the common light source 33 in identifying the medium to cause the specular reflection light from the recording medium M to be incident on the two-dimensional image sensor 26. Each of the optical path changing mirrors 34 and 35 is configured to be rotatable with a rotation axis as a fulcrum, and one surface thereof is a mirror face that reflects light. For example, the optical path changing mirror 34 is attached to the substrate 22 constituting the upper surface of the housing 23, and the optical path changing mirror 35 is attached to a side wall of the frame body 21 close to the opening 25. A color of a surface of the optical path changing mirror 35 opposite to the mirror face is, for example, black that absorbs light.

In the colorimetric camera 20A according to the first modification, the common light sources 33 are driven while the optical path changing mirrors 34 and 35 are in the state as illustrated in FIG. 30B, and the image of the colorimetric pattern is captured by the two-dimensional image sensor 26 under the illumination of the common light sources 33.

In identifying the medium, first, the common light sources 33 are driven while the optical path changing mirrors 34 and 35 are in the state as illustrated in FIG. 30B, and the image of the recording medium M is captured by the two-dimensional image sensor 26 under the illumination of the common light sources 33. Then, the image data of the diffused reflection region is acquired from the image of the recording medium M. Thereafter, each of the optical path changing mirrors 34 and 35 is rotated with the rotation axis as a fulcrum to be in the state as illustrated in FIG. 30A, and the common light sources 33 are driven. In this case, faces of the optical path changing mirrors 34 and 35 facing the common light source 33 are mirror faces. Accordingly, light from the common light source 33 is sequentially reflected by the optical path changing mirrors 34 and 35 to be emitted onto the recording medium M outside the housing 23. The specular reflection light that is regularly reflected by the recording medium M is incident on the two-dimensional image sensor 26. In this state, the image of the recording medium M is captured by the two-dimensional image sensor 26. The image data of the specular reflection region is then acquired from the image of the recording medium M.

The colorimetric camera 20A according to the first modification can identify the type of the recording medium M using the image data of the specular reflection region and the image data of the diffused reflection region that are acquired as described above through a method similar to that of the colorimetric camera 20.

Second Modification

Figure 31:
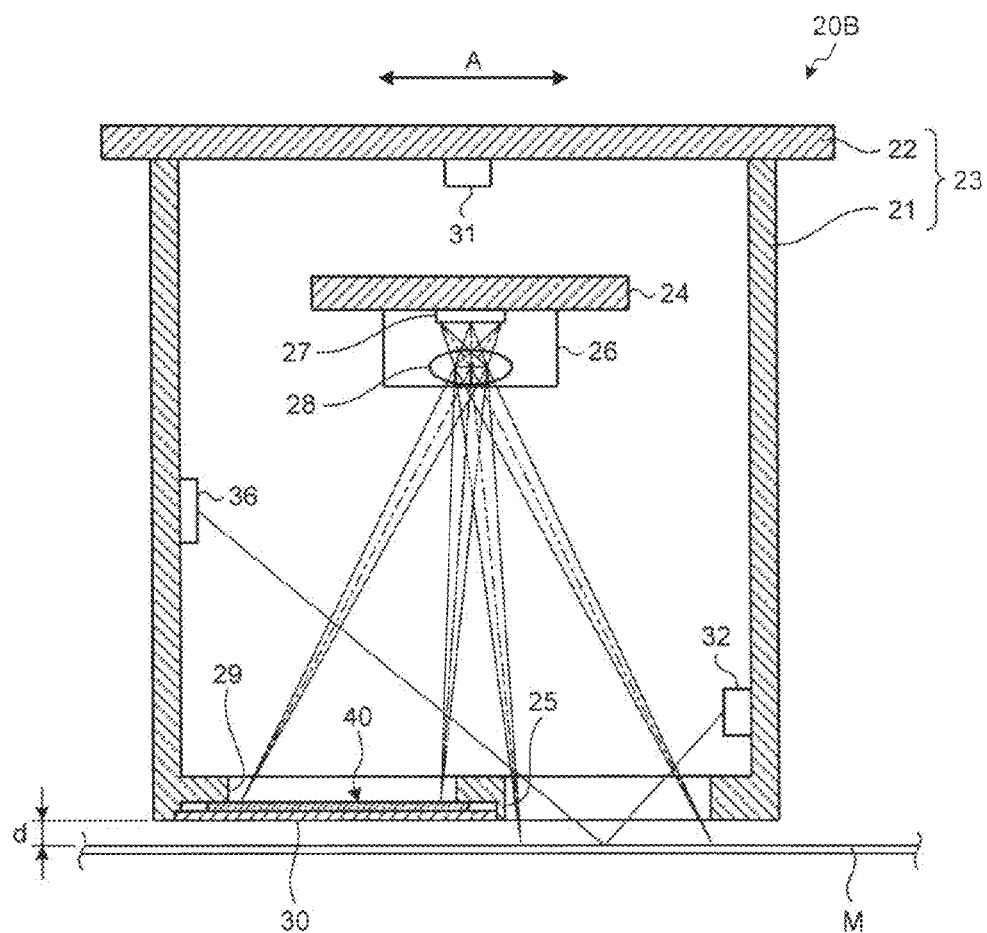
FIG. 31 is a vertical cross-sectional view of a colorimetric camera according to a second modification.

FIG. 31 is a vertical cross-sectional view of the colorimetric camera 20B according to the second modification. The colorimetric camera 20B according to the second modification includes a dedicated two-dimensional image sensor 36 used for acquiring the image data of the specular reflection region in identifying the medium in addition to the two-dimensional image sensor 26. In the colorimetric camera 20B according to the second modification, the second light source 32 is positioned so that the specular reflection light that is emitted from the second light source 32 and regularly reflected by the recording medium M outside the housing 23 is incident on the dedicated two-dimensional image sensor 36.

In identifying the medium, first, the colorimetric camera 20B according to the second modification captures the image of the recording medium M with the two-dimensional image sensor 26 under the illumination of the first light source 31, and acquires the image data of the diffused reflection region from the image of the recording medium M. Thereafter, the image of the recording medium M is captured by the dedicated two-dimensional image sensor 36 under the illumination of the second light source 32, and the image data of the specular reflection region is acquired from the image of the recording medium M. Thus, the type of the recording medium M can be identified using the image data of the specular reflection region and the image data of the diffused reflection region that are acquired as described above through a method similar to that of the colorimetric camera 20 described above.

The colorimetric camera 20B according to the second modification is configured to cause the specular reflection light from the recording medium M to be incident on the dedicated two-dimensional image sensor 36, so that the second light source 32 and the dedicated two-dimensional image sensor 36 can be relatively freely laid out.

Other Modifications

According to the embodiment described above, the colorimetric camera 20 has a function of identifying the type of the recording medium M. Alternatively, the type of the recording medium M may be identified outside the colorimetric camera 20 using the image of the recording medium M captured by the two-dimensional image sensor 26. For example, the CPU 101 or the FPGA for control 110 mounted on the main control board 120 of the image forming apparatus 100 can be configured to identify the type of the recording medium M. In this case, the colorimetric camera 20 is configured to transmit, to the CPU 101 or the FPGA for control 110, the image of the recording medium M captured by the two-dimensional image sensor 26 or the image data of the specular reflection region and the image data of the diffused reflection region extracted from the image in place of the medium information indicating the type of the recording medium M. That is, the colorimetric camera 20 is constructed as an image capturing unit without the function of identifying the type of the recording medium M.

Figure 32:
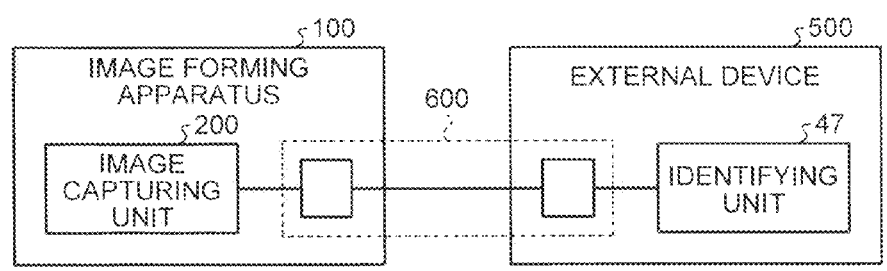
FIG. 32 is a diagram illustrating a schematic configuration of an image forming system.

According to the embodiment described above, the image forming apparatus 100 including the colorimetric camera 20 has the function of identifying the type of the recording medium M. However, the identification of the type of the recording medium M is not necessarily performed inside the image forming apparatus 100. For example, as illustrated in FIG. 32, an image forming system may be constructed in which the image forming apparatus 100 is connected to an external device 500 in a communicable manner, the external device 500 may be made to have a function as the identifying unit 47 for identifying the type of the recording medium M, and the colorimetric value may be calculated by the external device 500. That is, the image forming system is constructed to include an image capturing unit 200 (the configuration of which is the same as the colorimetric camera 20 excluding the identifying unit 47) arranged in the image forming apparatus 100, the identifying unit 47 arranged in the external device 500, and a communication module 600 that connects the image capturing unit 200 with the identifying unit 47 (connects the image forming apparatus 100 with the external device 500). As the external device 500, for example, a computer called a digital front end (DFE) can be used. As the communication module 600, communication utilizing a network such as a LAN or the Internet can be used in addition to wired or wireless P2P communication.

In a case of the above configuration, for example, the image forming apparatus 100 transmits, to the external device 500, the image of the recording medium M captured by the two-dimensional image sensor 26 of the image capturing unit 200, or the image data of the specular reflection region and the image data of the diffused reflection region extracted from the image utilizing the communication module 600. The external device 500 passes, to the identifying unit 47, the image of the recording medium M received from the image forming apparatus 100, or the image data of the specular reflection region and the image data of the diffused reflection region, and identifies the type of the recording medium M through the method described above. The external device 500 then transmits, to the image forming apparatus 100, the medium information indicating the type of the recording medium M identified by the identifying unit 47. The image forming apparatus 100 determines the discharging type of the ink to be discharged from the recording head 6 onto the recording medium M and the resolution of the image to be formed on the recording medium M based on the medium information received from the external device 500. Accordingly, the image forming apparatus 100 can perform optimum image formation on the recording medium M to be used.

In the above embodiment, the image forming apparatus 100 is described as the inkjet printer. Alternatively, the image forming apparatus 100 can be applied to an electrophotography device. When the image forming apparatus 100 is applied to the electrophotography device, a conveying speed or a transferring condition of the recording medium M, a temperature of a fixing device, and/or the like may be changed depending on the type of the recording medium M. Thereby, the image forming apparatus 100 can perform optimum image formation on the recording medium M to be used.

Control functions of the components constituting the image forming apparatus 100 and the colorimetric camera 20 according to the embodiment described above can be implemented as hardware, software, or a combination thereof. To implement the control functions of the components constituting the image forming apparatus 100 and the colorimetric camera 20 according to the embodiment as software, a processor included in the image forming apparatus 100 or the colorimetric camera 20 executes a computer program describing a processing sequence. The computer program executed by the processor is, for example, provided being incorporated in advance a ROM inside the image forming apparatus 100 or the colorimetric camera 20, and the like. The computer program executed by the processor may be recorded and provided in a computer-readable recording medium such as a compact disc read only memory (CD-ROM), a flexible disk (FD), a compact disc recordable (CD-R), and a digital versatile disc (DVD), as an installable or executable file.

The computer program executed by the processor may be stored in a computer connected to a network such as the Internet and provided by being downloaded via the network. Furthermore, the computer program executed by the processor may be provided or distributed via a network such as the Internet.

According to an embodiment, more variety of recording media than in the related art can be appropriately identified.

Although the invention has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

What is claimed is:

1. A medium identification device that identifies a type of a recording medium used for image formation, the medium identification device comprising:
    a two-dimensional image sensor that captures an image of the recording medium; and
    an identifying unit that obtains a glossiness evaluation value indicating glossiness of the recording medium, a surface roughness evaluation value indicating surface roughness of the recording medium, and a coloring evaluation value indicating coloring of the recording medium, using image data of a specular reflection region reflecting specular reflection light from the recording medium and image data of a diffused reflection region reflecting diffused reflection light from the recording medium, the regions being in the image of the recording medium, and identifies the type of the recording medium by combining determination using the glossiness evaluation value, determination using the surface roughness evaluation value, and determination using the coloring evaluation value.

2. The medium identification device according to claim 1, further comprising:
    a first light source arranged such that the specular reflection light from the recording medium is not incident on the two-dimensional image sensor; and
    a second light source arranged such that the specular reflection light from the recording medium is incident on the two-dimensional image sensor, wherein
    the identifying unit acquires the image data of the diffused reflection region from an image of the recording medium captured by the two-dimensional image sensor under illumination of the first light source, and acquires the image data of the specular reflection region from an image of the recording medium captured by the two-dimensional image sensor under illumination of the second light source.

3. The medium identification device according to claim 1, wherein the determination using the glossiness evaluation value includes processing of threshold determination of a peak value of a luminance histogram of the specular reflection region, and processing of threshold comparison of a value of a standard deviation of a histogram of a residual that is a difference between a luminance distribution in the specular reflection region and a normal distribution.

4. The medium identification device according to claim 1, wherein the determination using the surface roughness evaluation value is processing of threshold comparison of a value of a standard deviation of a luminance histogram of the diffused reflection region.

5. The medium identification device according to claim 1, wherein the determination using the coloring evaluation value is processing of collating a coordinate value of when a value representing a color of a pixel included in the diffused reflection region is plotted in a color space, with a coordinate range in the color space set for each type of a registered recording medium.

6. An image forming apparatus comprising the medium identification device according to claim 1.

7. The image forming apparatus according to claim 6, further comprising:
a recording head that discharges ink onto the recording medium; and
an ink discharge control unit that determines a discharging type of the ink discharged from the recording head and resolution of an image to be formed on the recording medium according to the type of the recording medium identified by the medium identification device.

8. The image forming apparatus according to claim 7, wherein the ink discharge control unit determines the discharging type and the resolution based on the type of the recording medium identified by the medium identification device and a designated printing mode.

9. The image forming apparatus according to claim 6, further comprising:
a notification unit that notifies a user that the recording medium is an unknown recording medium when the medium identification device has failed to identify the type of the recording medium.

10. The image forming apparatus according to claim 9, wherein the identifying unit generates information used for identifying the type of the unknown recording medium and stores the generated information in a storage unit in accordance with an operation by the user.

11. A method of identifying a medium executed by a medium identification device that comprises a two-dimensional image sensor, the method comprising:
capturing an image of a recording medium with the two-dimensional image sensor; and
obtaining a glossiness evaluation value indicating glossiness of the recording medium, a surface roughness evaluation value indicating surface roughness of the recording medium, and a coloring evaluation value indicating coloring of the recording medium, using image data of a specular reflection region reflecting specular reflection light from the recording medium and image data of a diffused reflection region reflecting diffused reflection light from the recording medium, the regions being in the image of the recording medium, and identifying a type of the recording medium by combining determination using the glossiness evaluation value, determination using the surface roughness evaluation value, and determination using the coloring evaluation value.

12. A computer program product comprising a non-transitory computer-readable medium containing an information processing program, the program causing a computer of a medium identification device that comprises a two-dimensional image sensor, to implement:
a function of capturing an image of a recording medium with the two-dimensional image sensor; and
a function of obtaining a glossiness evaluation value indicating glossiness of the recording medium, a surface roughness evaluation value indicating surface roughness of the recording medium, and a coloring evaluation value indicating coloring of the recording medium, using image data of a specular reflection region reflecting specular reflection light from the recording medium and image data of a diffused reflection region reflecting diffused reflection light from the recording medium, the regions being in the image of the recording medium, and identifying a type of the recording medium by combining determination using the glossiness evaluation value, determination using the surface roughness evaluation value, and determination using the coloring evaluation value.

* * * * *